(12) United States Patent
DiLillo et al.

(10) Patent No.: US 12,150,959 B2
(45) Date of Patent: Nov. 26, 2024

(54) CHIMERIC ANTIGEN RECEPTORS WITH BCMA SPECIFICITY AND USES THEREOF

(71) Applicant: Regeneron Pharmaceuticals, Inc., Tarrytown, NY (US)

(72) Inventors: David DiLillo, New York, NY (US); Frank Delfino, Poughquag, NY (US); Kevin Bray, Garnerville, NY (US); Thomas Craig Meagher, Yorktown Heights, NY (US); Jessica Kirshner, New York, NY (US); Olga Sineshchekova, Pleasantville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1397 days.

(21) Appl. No.: 16/516,060

(22) Filed: Jul. 18, 2019

(65) Prior Publication Data

US 2020/0023010 A1    Jan. 23, 2020

Related U.S. Application Data

(60) Provisional application No. 62/700,615, filed on Jul. 19, 2018.

(51) Int. Cl.
| | | |
|---|---|---|
| *C07K 14/725* | (2006.01) | |
| *A61K 35/17* | (2015.01) | |
| *A61K 39/00* | (2006.01) | |
| *A61P 35/02* | (2006.01) | |
| *C07K 14/705* | (2006.01) | |
| *C07K 16/28* | (2006.01) | |
| *C12N 5/0783* | (2010.01) | |
| *C12N 15/85* | (2006.01) | |

(52) U.S. Cl.
CPC .......... *C07K 14/7051* (2013.01); *A61K 35/17* (2013.01); *A61K 39/4611* (2023.05); *A61K 39/4631* (2023.05); *A61K 39/464417* (2023.05); *A61P 35/02* (2018.01); *C07K 14/70517* (2013.01); *C07K 16/2827* (2013.01); *C07K 16/2878* (2013.01); *C12N 5/0636* (2013.01); *C12N 15/85* (2013.01); *A61K 2239/13* (2023.05); *A61K 2239/31* (2023.05); *A61K 2239/38* (2023.05); *A61K 2239/48* (2023.05)

(58) Field of Classification Search
None
See application file for complete search history.

(56) References Cited

U.S. PATENT DOCUMENTS

| | | |
|---|---|---|
| 6,737,056 B1 | 5/2004 | Presta |
| 7,083,785 B2 | 8/2006 | Browning et al. |
| 7,261,893 B2 | 8/2007 | Veldman et al. |
| 7,691,804 B2 | 4/2010 | Jeffrey et al. |
| 7,700,099 B2 | 4/2010 | Strohl |
| 8,193,322 B2 | 6/2012 | Yan et al. |
| 8,323,962 B2 | 12/2012 | Dall'Acqua et al. |
| 8,920,776 B2 | 12/2014 | Gaiger et al. |
| 9,034,324 B2 | 5/2015 | Kalled et al. |
| 9,150,664 B2 | 10/2015 | Kufer et al. |
| 9,243,058 B2 | 1/2016 | Armitage et al. |
| 9,273,141 B2 | 3/2016 | Algate et al. |
| 9,340,621 B2 | 5/2016 | Kufer et al. |
| 9,598,500 B2 | 3/2017 | Kufer et al. |
| 9,650,430 B2 | 5/2017 | Browning et al. |
| 9,657,102 B2 | 5/2017 | Smith et al. |
| 9,963,513 B2 | 5/2018 | Vu et al. |
| 9,969,809 B2 | 5/2018 | Kuo et al. |
| 10,040,860 B2 | 8/2018 | Kuo et al. |
| 10,072,088 B2 | 9/2018 | Pillarisetti et al. |
| 10,077,315 B2 | 9/2018 | Vu et al. |
| 10,144,782 B2 | 12/2018 | Oden et al. |
| 10,189,906 B2 | 1/2019 | Lipp et al. |
| 10,220,090 B2 | 3/2019 | Armitage et al. |
| 10,253,104 B2 | 4/2019 | Vu et al. |

(Continued)

FOREIGN PATENT DOCUMENTS

| | | |
|---|---|---|
| AU | 2013340799 B2 | 11/2013 |
| EP | 1975231 B1 | 8/2011 |

(Continued)

OTHER PUBLICATIONS

Dilillo et al., "REGN5458, a Bispecific BCMAxCD3 T Cell Engaging Antibody, Demonstrates Robust in Vitro and In Vivo Anti-Tumor Efficacy in Multiple Myeloma Models, Comparable to that of BCMA CAR T Cells," Myeloma: Pathophysiology and Preclinical studies, excluding therapy: poster I, Article 132: 1-5 (2018). XP-002794959.

(Continued)

*Primary Examiner* — Michael D Burkhart

(74) *Attorney, Agent, or Firm* — Schwabe, Williamson & Wyatt PC; Gabe Amodeo

(57) ABSTRACT

B-cell maturation antigen (BCMA) is expressed on malignant plasma cells. The present invention provides BCMA-specific chimeric antigen receptors and cells expressing such chimeric antigen receptors. In certain embodiments, engineered cells expressing the chimeric antigen receptors of the present invention are capable of inhibiting the growth of tumors expressing BCMA. The engineered cells of the invention are useful for the treatment of diseases and disorders in which an upregulated or induced BCMA-targeted immune response is desired and/or therapeutically beneficial. For example, engineered cells expressing the BCMA-specific chimeric antigen receptors of the invention are useful for the treatment of various cancers, including multiple myeloma.

25 Claims, 1 Drawing Sheet
Specification includes a Sequence Listing.

(56) References Cited

U.S. PATENT DOCUMENTS

| | | |
|---|---|---|
| 11,384,153 B2 | 7/2022 | Smith et al. |
| 2005/0244374 A1 | 11/2005 | Goebel et al. |
| 2013/0273055 A1 | 10/2013 | Borges et al. |
| 2014/0112914 A1 | 4/2014 | Nezu et al. |
| 2015/0023967 A1 | 1/2015 | Kufer et al. |
| 2015/0344583 A1 | 12/2015 | Armitage et al. |
| 2016/0176973 A1 | 6/2016 | Kufer et al. |
| 2017/0051074 A1 | 2/2017 | Kirshner et al. |
| 2017/0165373 A1 | 6/2017 | Armitage et al. |
| 2017/0209571 A1 | 7/2017 | Kanapuram et al. |
| 2017/0218077 A1 | 8/2017 | Raum et al. |
| 2017/0233484 A1 | 8/2017 | Sussman et al. |
| 2017/0253670 A1 | 9/2017 | Klein et al. |
| 2017/0327580 A1 | 11/2017 | Vu et al. |
| 2018/0030148 A1 | 2/2018 | Algate et al. |
| 2018/0112384 A1 | 4/2018 | Rothleitner et al. |
| 2018/0118842 A1 | 5/2018 | Brentjens et al. |
| 2018/0147293 A1 | 5/2018 | Algate et al. |
| 2018/0171018 A1 | 6/2018 | Kuo et al. |
| 2018/0194850 A1 | 7/2018 | Faustman |
| 2018/0222991 A1 | 8/2018 | Vu et al. |
| 2018/0273605 A1 | 9/2018 | Browning et al. |
| 2018/0298108 A1 | 10/2018 | Kuo et al. |
| 2018/0360880 A1 | 12/2018 | Brentjens et al. |
| 2019/0023801 A1 | 1/2019 | Sussman et al. |
| 2019/0040152 A1 | 2/2019 | Kinneer et al. |
| 2019/0106499 A1 | 4/2019 | Lipp et al. |
| 2019/0112381 A1 | 4/2019 | Wesche et al. |
| 2019/0112382 A1 | 4/2019 | Oden et al. |
| 2019/0161552 A1 | 5/2019 | Kalled et al. |
| 2020/0048349 A1 | 2/2020 | Gaudet et al. |
| 2020/0345843 A1 | 11/2020 | Asrat et al. |

FOREIGN PATENT DOCUMENTS

| | | |
|---|---|---|
| EP | 2762496 A1 | 8/2014 |
| EP | 2762497 A1 | 8/2014 |
| EP | 2465871 B1 | 5/2015 |
| EP | 1210425 B2 | 6/2015 |
| EP | 1957533 B1 | 7/2015 |
| EP | 2982692 A1 | 2/2016 |
| EP | 1806143 B1 | 6/2016 |
| EP | 2982694 B1 | 6/2016 |
| EP | 3029068 A1 | 8/2016 |
| EP | 2552955 B1 | 5/2017 |
| EP | 2953974 B1 | 12/2017 |
| EP | 2647707 B1 | 9/2018 |
| EP | 3415531 A1 | 12/2018 |
| EP | 2780374 B1 | 8/2019 |
| EP | 2780375 B1 | 9/2019 |
| EP | 3572427 A1 | 11/2019 |
| EP | 3689908 A2 | 8/2020 |
| WO | 12/066058 A1 | 5/2012 |
| WO | 12/163805 A1 | 12/2012 |
| WO | 13/072406 A1 | 5/2013 |
| WO | 13/072415 A1 | 5/2013 |
| WO | 14/047231 A1 | 3/2014 |
| WO | 14/068079 A1 | 5/2014 |
| WO | 14/089335 A2 | 6/2014 |
| WO | 14/122143 A1 | 8/2014 |
| WO | 14/140248 A1 | 9/2014 |
| WO | 15/166073 A1 | 11/2015 |
| WO | 16/087531 A1 | 6/2016 |
| WO | 16/090327 A2 | 6/2016 |
| WO | 2016/094304 A2 | 6/2016 |
| WO | 16/166629 A1 | 10/2016 |
| WO | 16/166630 A1 | 10/2016 |
| WO | 17/031104 A1 | 2/2017 |
| WO | 2017/053856 A1 | 3/2017 |
| WO | 17/083511 A1 | 5/2017 |
| WO | 17/093942 A1 | 6/2017 |
| WO | 17/129585 A1 | 8/2017 |
| WO | 17/143069 A1 | 8/2017 |
| WO | 2017/173349 A1 | 10/2017 |
| WO | 2017/211900 A1 | 12/2017 |
| WO | 18/009904 A2 | 1/2018 |
| WO | 18/052503 A1 | 3/2018 |
| WO | 18/067331 A1 | 4/2018 |
| WO | 18/075359 A1 | 4/2018 |
| WO | 18/083204 A1 | 5/2018 |
| WO | 18/099978 A1 | 6/2018 |
| WO | 18/119215 A9 | 6/2018 |
| WO | 18/145075 A1 | 8/2018 |
| WO | 18/151836 A1 | 8/2018 |
| WO | 18/201051 A1 | 11/2018 |
| WO | 18/204907 A1 | 11/2018 |
| WO | 18/237037 A2 | 12/2018 |
| WO | PCT/US2019/042452 | 7/2019 |
| WO | 19/149249 A1 | 8/2019 |
| WO | 2020/191346 A1 | 9/2020 |

OTHER PUBLICATIONS

Harrington et al., "Development of JCARH125: Optimization of a Fully Human Anti-Bcma CAR for Use in the Treatment of Multiple Myeloma," Blood 130 (Suppl. 1): 1813, 1-2 (2017). XP-002795011.

Smith et al., "Development and Evaluation of an Optimal Human Single-Chain Variable Fragment-Derived BCMA-Targeted CAR T Cell Vector," Molecular Therapy, vol. 26(No. 6) 1447-1456 (2018). XP-002795010.

WIPO Application No. PCT/US2019/042447, Invitation to Pay Additional Fees and, where applicable, Protest Fee dated Oct. 23, 2019.

WIPO Application No. PCT/US2019/042452, Invitation to Pay Additional Fees and, where applicable, Protest Fee dated Oct. 25, 2019.

WIPO Application No. PCT/US2019/042452, PCT International Search Report and Written Opinion of the International Searching Authority dated Nov. 22, 2019.

WIPO Application No. PCT/US2019/042447, PCT International Search Report and Written Opinion of the International Searching Authority dated Dec. 20, 2019.

U.S. Appl. No. 67/700,615, filed Jul. 19, 2018, Expired.

Abramson, "The Multiple Myeloma Drug Pipeline-2018: A Review of Small Molecules and Their Therapeutic Targets," The Multiple Myeloma Drug Pipeline, 1-19, (2018).

Bluhm et al., "CAR T Cells with Enhanced Sensitivity to B Cell Maturation Antigen for the Targeting of B Cell Non-Hodgkin's Lymphoma and Multiple Myeloma," American Society of Gene & Cell Therapy, Molecular Therapy, vol. 26 No. 8; 1-15 (2018). [https://doi.org/10.1016/j.ymthe.2018.06.012].

Hoffman et al., "B Cells, Antibodies, and More," American Society of Nephrology, vol. 11: 137-154 (2016). Doi: 10.2215/CJN.09430915.

Tai et al., "Targeting B-cell maturation antigen in multiple myeloma," Future Medicine: Immunotherapy, vol. 7(11): 1187-1199 (2015).

U.S. Appl. No. 16/516,028, Requirement for Restriction/Election dated May 14, 2021.

U.S. Appl. No. 16/516,028, Non-Final Office Action dated Sep. 14, 2021.

U.S. Appl. No. 16/516,028, Notice of Allowance dated Feb. 28, 2022.

U.S. Appl. No. 62/700,615, filed Jul. 19, 2018.

PCT/US2019/042452, Jul. 18, 2019, WO 2020/018825, Expired.

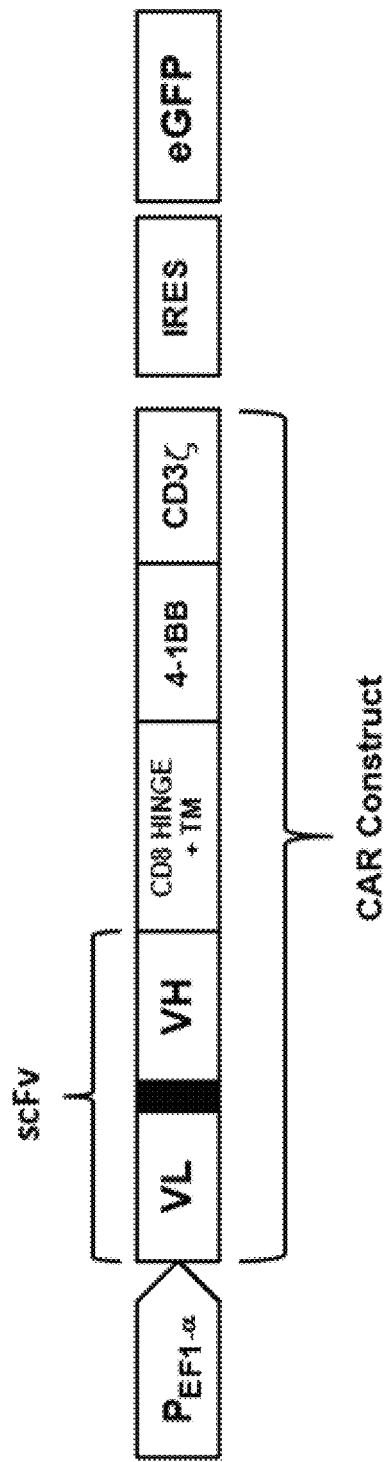

CHIMERIC ANTIGEN RECEPTORS WITH BCMA SPECIFICITY AND USES THEREOF

CROSS-REFERENCE TO RELATED APPLICATIONS

This application claims the benefit under 35 USC § 119(e) of U.S. Provisional Application No. 62/700,615, filed Jul. 19, 2018, which is incorporated herein by reference in its entirety for all purposes.

REFERENCE TO A SEQUENCE LISTING

This application incorporates by reference the Sequence Listing submitted in Computer Readable Form as file 10455US01-Sequence.txt, created on Jul. 16, 2019 and containing 66,907 bytes.

FIELD OF THE INVENTION

The present invention relates to chimeric antigen receptors (CARs), and engineered cells comprising such CARs, which are specific for B-cell maturation antigen (BCMA), and methods of use thereof.

BACKGROUND

B-cell maturation antigen (BCMA), also known as TNFRSF17, or CD269, is a type III transmembrane protein lacking a signal peptide and containing a cysteine-rich extracellular domain. BCMA, along with closely related proteins, promotes B-cell survival at distinct stages of development. BCMA is expressed exclusively in B-cell lineage cells, particularly in the interfollicular region of the germinal center as well as on plasmablasts and differentiated plasma cells. BCMA is selectively induced during plasma cell differentiation, and is required for optimal survival of long-lived plasma cells in the bone marrow. In multiple myeloma, BCMA is widely expressed on malignant plasma cells at elevated levels, and BCMA expression is increased with progression from normal cells to active multiple myeloma. BCMA is also expressed in other B-cell malignancies, including Waldenström's macroglobulinemia, Burkitt lymphoma, and Diffuse Large B-Cell Lymphoma. Tai et al., *Immunotherapy*, 7(11):1187-1199, 2015.

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and heavy chain variable fragments of a monoclonal antibody joined by a flexible linker. The signaling domains for first generation CARs are derived from the cytoplasmic region of the CD3zeta or the Fc receptor gamma chains. First generation CARs have been shown to successfully redirect T-cell cytotoxicity. However, they failed to provide prolonged expansion and anti-tumor activity in vivo. Signaling domains from co-stimulatory molecules, as well as transmembrane and hinge domains have been added to form CARs of second and third generations, leading to some successful therapeutic trials in humans. For example, CAR redirected T cells specific for the B cell differentiation antigen CD19 have shown dramatic efficacy in the treatment of B cell malignancies, while TCR-redirected T cells have shown benefits in patients suffering from solid cancer. Stauss et al. describe strategies to modify therapeutic CARs and TCRs, for use in the treatment of cancer, for example, to enhance the antigen-specific effector function and limit toxicity of engineered T cells (*Current Opinion in Pharmacology* 2015, 24:113-118).

Engineered cells expressing chimeric antigen receptors that target BCMA would be useful in therapeutic settings in which specific targeting and T cell-mediated killing of cells that express BCMA is desired.

BRIEF SUMMARY OF THE INVENTION

In one aspect, the present invention provides a B-cell maturation antigen (BCMA)-specific chimeric antigen receptor comprising, from N-terminus to C-terminus: (a) an extracellular ligand-binding domain comprising an anti-BCMA antigen-binding domain; (b) a hinge; (c) a transmembrane domain; and (d) a cytoplasmic domain comprising a costimulatory domain and a signaling domain.

In some cases, the extracellular ligand-binding domain comprises an anti-BCMA single chain variable fragment (scFv) domain comprising a light chain variable region (LCVR) and a heavy chain variable region (HCVR). In some embodiments, the anti-BCMA scFv domain comprises a linker between the LCVR and the HCVR. In some cases, the chimeric antigen receptor further comprises a linker between the extracellular ligand-binding domain (e.g., the scFv domain) and the hinge. In some cases, the linker comprises an amino acid sequence selected from the group consisting of SEQ ID NOs: 93-96. In some embodiments, the linker is a $(G4S)_n$ linker, wherein n is 1-10.

In some cases, the hinge, the transmembrane domain, or both, are from a CD8α polypeptide. In some cases, the costimulatory domain comprises a 4-1BB costimulatory domain. In some cases, the signaling domain comprises a CD3zeta signaling domain. In some embodiments, the hinge comprises the amino acid sequence of SEQ ID NO: 97. In some embodiments, the transmembrane domain comprises the amino acid sequence of SEQ ID NO: 98. In some embodiments, the 4-1BB costimulatory domain comprises the amino acid sequence of SEQ ID NO: 99. In some embodiments, the CD3zeta signaling domain comprises the amino acid sequence of SEQ ID NO: 100.

In some cases, the LCVR comprises the complementarity determining regions (CDRs) of a LCVR comprising an amino acid sequence selected from the group consisting of SEQ ID NOs: 10, 26, 42, 58 and 74. In some cases, the LCVR comprises LCDR1-LCDR2-LCDR3 domains comprising the amino acid sequences, respectively, of SEQ ID NOs: 12-14-16, 28-30-32, 44-46-48, 60-62-64, or 76-78-80. In some cases, the HCVR comprises the CDRs of a HCVR comprising an amino acid sequence selected from the group consisting of SEQ ID NOs: 2, 18, 34, 50 and 66. In some cases, the HCVR comprises HCDR1-HCDR2-HCDR3 domains comprising the amino acid sequences, respectively, of SEQ ID NOs: 4-6-8, 20-22-24, 36-38-40, 52-54-56, or 68-70-72.

In some embodiments, the LCVR comprises an amino acid sequence selected from the group consisting of SEQ ID NOs: 10, 26, 42, 58 and 74, or an amino acid sequence having 95%-99% sequence identity to an amino acid sequence selected from the group consisting of SEQ ID NOs: 10, 26, 42, 58 and 74; and the HCVR comprises an amino acid sequence selected from the group consisting of SEQ ID NOs: 2, 18, 34, 50 and 66, or an amino acid sequence having 95%-99% sequence identity to an amino acid sequence selected from the group consisting of SEQ ID NOs: 2, 18, 34, 50 and 66. In some cases, the LCVR comprises an amino acid sequence selected from the group consisting of SEQ ID NOs: 10, 26, 42, 58 and 74, and the HCVR comprises an amino acid sequence selected from the group consisting of SEQ ID NOs: 2, 18, 34, 50 and 66.

In some embodiments, the scFv domain comprises a LCVR/HCVR amino acid sequence pair comprising the amino acid sequences of SEQ ID NOs: 10/2, 26/18, 42/34, 58/50, or 74/66. In some cases, the LCVR and HCVR are joined by a linker, optionally a (G4S)$_n$ linker in which n=1-3.

In some cases, the chimeric antigen receptor comprises the amino acid sequence of SEQ ID NO: 82, SEQ ID NO: 84, SEQ ID NO: 86, SEQ ID NO: 88, or SEQ ID NO: 90. In some embodiments, the chimeric antigen receptor comprises the amino acid sequence of SEQ ID NO: 82. In some embodiments, the chimeric antigen receptor comprises the amino acid sequence of SEQ ID NO: 84. In some embodiments, the chimeric antigen receptor comprises the amino acid sequence of SEQ ID NO: 86. In some embodiments, the chimeric antigen receptor comprises the amino acid sequence of SEQ ID NO: 88. In some embodiments, the chimeric antigen receptor comprises the amino acid sequence of SEQ ID NO: 90.

In another aspect, the present invention provides an isolated nucleic acid molecule encoding a chimeric antigen receptor discussed above or herein. In some cases, the nucleic acid molecule comprises a nucleotide sequence selected from the group consisting of SEQ ID NO: 81, 83, 85, 87 and 89.

In another aspect, the present invention provides a vector comprising a nucleic acid molecule discussed above or herein. In some cases, the vector is a DNA vector, an RNA vector, a plasmid, a lentivirus vector, an adenovirus vector, or a retroviral vector. In some embodiments, the vector is a lentivirus vector.

In another aspect, the present invention provides a cell comprising a nucleic acid molecule, or a vector discussed above or herein. In some cases, the cell is a human T cell.

In another aspect, the present invention provides an engineered cell comprising a chimeric antigen receptor as discussed above or herein. In some cases, the engineered cell is an immune cell. In some cases, the immune cell is an immune effector cell. In some cases, the immune effector cell is a T lymphocyte. In some embodiments, the T lymphocyte is an inflammatory T lymphocyte, a cytotoxic T lymphocyte, a regulatory T lymphocyte, or a helper T lymphocyte. In some embodiments, the engineered cell is a CD8+ cytotoxic T lymphocyte.

In some cases, the engineered cells of the present invention are for use in the treatment of a BCMA-expressing cancer. In some cases, the BCMA-expressing cancer is multiple myeloma.

In another aspect, the present invention provides an engineered human T cell comprising a chimeric antigen receptor comprising, from N-terminus to C-terminus: (a) an extracellular ligand-binding domain comprising an anti-BCMA single chain variable fragment (scFv) domain comprising a light chain variable region (LCVR) and a heavy chain variable region (HCVR); (b) a hinge; (c) a transmembrane domain; and (d) a cytoplasmic domain comprising a 4-1BB costimulatory domain and a CD3zeta signaling domain.

In some cases, the scFv domain comprises a LCVR/HCVR amino acid sequence pair comprising the amino acid sequences of SEQ ID NOs: 10/2, 26/18, 42/34, 58/50, or 74/66. In some cases, the hinge comprises the amino acid sequence of SEQ ID NO: 97. In some cases, the transmembrane domain comprises the amino acid sequence of SEQ ID NO: 98. In some cases, the 4-1BB costimulatory domain comprises the amino acid sequence of SEQ ID NO: 99. In some cases, the CD3zeta signaling domain comprises the amino acid sequence of SEQ ID NO: 100.

In some embodiments, the engineered human T cell comprises a chimeric antigen receptor comprising the amino acid sequence of SEQ ID NO: 82. In some embodiments, the engineered human T cell comprises a chimeric antigen receptor comprising the amino acid sequence of SEQ ID NO: 84. In some embodiments, the engineered human T cell comprises a chimeric antigen receptor comprising the amino acid sequence of SEQ ID NO: 86. In some embodiments, the engineered human T cell comprises a chimeric antigen receptor comprising the amino acid sequence of SEQ ID NO: 88. In some embodiments, the engineered human T cell comprises a chimeric antigen receptor comprising the amino acid sequence of SEQ ID NO: 90.

In another aspect, the present invention provides a pharmaceutical composition comprising a genetically-modified human T cell and a pharmaceutically acceptable carrier, wherein the genetically-modified human T cell comprises a chimeric antigen receptor as discussed above or herein. In some cases, the pharmaceutical composition is for use in the treatment of a BCMA-expressing cancer. In some embodiments, the BCMA-expressing cancer is multiple myeloma.

In another aspect, the present invention provides an engineered cell as discussed above or herein. In some cases, the pharmaceutical composition is for use in the treatment of a BCMA-expressing cancer. In some embodiments, the BCMA-expressing cancer is multiple myeloma.

In another aspect, the present invention provides use of a chimeric antigen receptor, a nucleic acid molecule, a vector, a cell, or an engineered cell as discussed above or herein in the manufacture of a medicament for the treatment of a BCMA-expressing cancer. In some cases, the BCMA-expressing cancer is multiple myeloma. In various embodiments, the chimeric antigen receptors, nucleic acid molecules, vectors, cells, or engineered cells discussed above or herein are contemplated for use in any of the methods discussed above or herein. For example, in some embodiments, the CARs or engineered cells discussed herein are for use in medicine or for use in the treatment of cancer as discussed above or herein.

In another aspect, the present invention provides a method of enhancing T lymphocyte activity in a subject comprising, introducing into the subject a T lymphocyte comprising a chimeric antigen receptor as discussed above or herein.

In another aspect, the present invention provides a method for treating a subject suffering from cancer comprising, introducing into the subject a therapeutically effective amount of a T lymphocyte comprising a chimeric antigen receptor as discussed above or herein.

In another aspect, the present invention provides a method for stimulating a T cell-mediated immune response to a target cell population or tissue in a subject comprising, administering to the subject an effective amount of a cell genetically modified to express a chimeric antigen receptor as discussed above or herein.

In another aspect, the present invention provides a method of providing anti-tumor immunity in a subject, the method comprising administering to the subject an effective amount of a cell genetically modified to express a chimeric antigen receptor as discussed above or herein.

In some embodiments of the methods discussed above, the subject is a human. In some cases, the subject is suffering from multiple myeloma, B lineage acute lymphoblastic leukemia, B-cell chronic lymphocytic leukemia, B-cell non-Hodgkin's lymphoma, leukemia and lymphoma, acute lymphoblastic leukemia, Hodgkin's lymphoma, or childhood acute lymphoblastic leukemia. In some embodiments, the subject is suffering from multiple myeloma.

In another aspect, the present invention provides a method of engineering a population of cells to express a chimeric antigen receptor, in which the method comprises: (a) providing a population of immune cells; (b) introducing into the immune cells a nucleic acid molecule encoding a chimeric antigen receptor as discussed above or herein; (c) culturing the immune cells under conditions to express the nucleic acid molecules; and (d) isolating the immune cells expressing the chimeric antigen receptor at the cells' surface. In some cases, the method further comprises obtaining the population of immune cells from a subject prior to introducing the nucleic acid molecule.

In another aspect, the present invention provides a method of treating a BCMA-expressing cancer in a subject, in which the method comprises: (a) engineering a population of cells according to the method discussed above; and (b) reintroducing the population of immune cells expressing the chimeric antigen receptors into the subject. In some embodiments, the BCMA-expressing cancer is multiple myeloma.

Other embodiments will become apparent from a review of the ensuing detailed description.

BRIEF DESCRIPTION OF THE DRAWINGS

FIG. 1 illustrates an exemplary nucleotide construct for expressing a chimeric antigen receptor (CAR) construct. The exemplary nucleotide construct comprises an anti-BCMA VL-linker-VH scFv, a human CD8 hinge and transmembrane domain, a 4-1BB co-stimulatory domain, a CD3zeta signaling domain, and an IRES:eGFP sequence for tracking CAR-transduced cells.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention. Any specific value discussed above or herein may be combined with another related value discussed above or herein to recite a range with the values representing the upper and lower ends of the range, and such ranges are encompassed within the scope of the present disclosure.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "BCMA," as used herein, refers to B-cell maturation antigen. BCMA (also known as TNFRSF17 and CD269) is a cell surface protein expressed on malignant plasma cells, and plays a central role in regulating B cell maturation and differentiation into immunoglobulin-producing plasma cells. As used herein, "BCMA" refers to the human BCMA protein unless specified as being from a non-human species (e.g., "mouse BCMA," "monkey BCMA," etc.). The human BCMA protein has the amino acid sequence shown in SEQ ID NO: 101.

As used herein, "an antibody that binds BCMA" or an "anti-BCMA antibody" includes antibodies and antigen-binding fragments thereof that specifically recognize BCMA.

The terms "ligand-binding domain" and "antigen-binding domain" are used interchangeably herein, and refer to that portion of a chimeric antigen receptor or a corresponding antibody that binds specifically to a predetermined antigen (e.g., BCMA). References to a "corresponding antibody" refer to the antibody from which the CDRs or variable regions (HCVR and LCVR) used in a chimeric antigen receptor are derived. For example, chimeric antigen receptor constructs discussed in Example 2 include scFvs with variable regions derived from specific anti-BCMA antibodies. These anti-BCMA antibodies are the "corresponding antibodies" to the respective chimeric antigen receptors.

The term "antibody", as used herein, means any antigen-binding molecule or molecular complex comprising at least one complementarity determining region (CDR) that specifically binds to or interacts with a particular antigen (e.g., BCMA). The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-BCMA antibody (or antigen-binding portion thereof)

may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

In certain embodiments, the anti-BCMA antibodies are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-BCMA antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The anti-BCMA antibodies may comprise variants of any of the HCVR, LCVR, and/or CDR amino acid sequences disclosed herein having one or more conservative substitutions. For example, the anti-BCMA antibodies may have HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine;

(6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-3402, each herein incorporated by reference.

As used herein, the terms "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

The term "chimeric antigen receptor" (CAR) refers to molecules that combine a binding domain against a component present on the target cell, for example an antibody-based specificity for a desired antigen (e.g., a tumor antigen, such as BCMA) with a T cell receptor-activating intracellular domain to generate a chimeric protein that exhibits a specific anti-target cellular immune activity. Generally, CARs consist of an extracellular single chain antibody-binding domain (scFv) fused to the intracellular signaling domain of the T cell antigen receptor complex zeta chain, and have the ability, when expressed in T cells, to redirect antigen recognition based on the monoclonal antibody's specificity.

The term "vector," as used herein, includes, but is not limited to, a viral vector, a plasmid, an RNA vector or a linear or circular DNA or RNA molecule which may consists of chromosomal, non-chromosomal, semi-synthetic or synthetic nucleic acids. In some cases, the vectors are those capable of autonomous replication (episomal vector) and/or expression of nucleic acids to which they are linked (expression vectors). Large numbers of suitable vectors are known to those of skill in the art and are commercially available. Viral vectors include retrovirus, adenovirus, parvovirus (e.g., adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, and lentivirus.

A "costimulatory domain" or "costimulatory molecule" refers to the cognate binding partner on a T-cell that specifically binds with a costimulatory ligand, thereby mediating a costimulatory response by the cell, such as, but not limited to proliferation. Costimulatory molecules include, but are not limited to, an MHC class I molecule, BTLA and Toll ligand receptor. Examples of costimulatory molecules include CD27, CD28, CD8, 4-1BB (CD137) (SEQ ID NO: 99), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like. A costimulatory molecule is a cell surface molecule other than an antigen receptor or their ligands that is required for an efficient immune response.

A "costimulatory ligand" refers to a molecule on an antigen presenting cell that specifically binds a cognate costimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A costimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3.

A "costimulatory signal" refers to a signal, which in combination with a primary signal, such as TCR/CD3 ligation, leads to T cell proliferation and/or upregulation or downregulation of key molecules.

The term "extracellular ligand-binding domain," as used herein, refers to an oligo- or polypeptide that is capable of binding a ligand, e.g., a cell surface molecule. For example, the extracellular ligand-binding domain may be chosen to recognize a ligand that acts as a cell surface marker on target cells associated with a particular disease state (e.g., cancer). Examples of cell surface markers that may act as ligands include those associated with viral, bacterial and parasitic infections, autoimmune disease and cancer cells.

The term "subject" or "patient" as used herein includes all members of the animal kingdom including non-human primates and humans. In one embodiment, patients are humans with a cancer (e.g., multiple myeloma).

A "signal transducing domain" or "signaling domain" of a CAR, as used herein, is responsible for intracellular signaling following the binding of an extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector function signal and directs the cell to perform a specialized function. Examples of signal transducing domains for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. In some cases, signaling domains comprise two distinct classes of cytoplasmic signaling sequences, those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Exemplary ITAMs include those derived from TCRzeta, FcRgamma, FcRbeta, FcRepsilon, CD3gamma, CD3delta, CD3epsilon, CD5, CD22, CD79a, CD79b and CD66d. In some embodiments, the signal transducing domain of the CAR can comprise the CD3zeta signaling domain (SEQ ID NO: 100).

Chimeric Antigen Receptors (CARs)

Chimeric antigen receptors (CARs) redirect T cell specificity toward antibody-recognized antigens expressed on the surface of cells (e.g., cancer cells), while T cell receptors (TCRs) extend the range of targets to include intracellular antigens (e.g., tumor antigens).

One aspect of the present invention includes a chimeric antigen receptor (CAR) which is specific for a B-Cell Maturation Antigen (BCMA) expressed on the surface of malignant plasma cells. In one embodiment of the present invention, a CAR as described herein comprises an extracellular target-specific binding domain, a transmembrane domain, an intracellular signaling domain (such as a signaling domain derived from CD3zeta or FcRgamma), and/or one or more co-stimulatory signaling domains derived from a co-stimulatory molecule, such as, but not limited to, 4-1BB. In one embodiment, the CAR includes a hinge or spacer region between the extracellular binding domain and the transmembrane domain, such as a CD8alpha hinge.

The binding domain or the extracellular domain of the CAR provides the CAR with the ability to bind to the target antigen of interest. A binding domain (e.g., a ligand-binding domain or antigen-binding domain) can be any protein, polypeptide, oligopeptide, or peptide that possesses the ability to specifically recognize and bind to a biological molecule (e.g., a cell surface receptor or tumor protein, or a component thereof). A binding domain includes any naturally occurring, synthetic, semi-synthetic, or recombinantly produced binding partner for a biological molecule of interest. For example, and as further described herein, a binding domain may be antibody light chain and heavy chain variable regions, or the light and heavy chain variable regions can be joined together in a single chain and in either orientation (e.g., $V_L$-$V_H$ or $V_H$-$V_L$). A variety of assays are known for identifying binding domains of the present disclosure that specifically bind with a particular target, including Western blot, ELISA, flow cytometry, or surface plasmon resonance analysis (e.g., using BIACORE analysis). The target may be an antigen of clinical interest against which it would be desirable to trigger an effector immune response that results in tumor killing. In one embodiment, the target antigen of the binding domain of the chimeric antigen receptor is a BCMA protein on the surface of tumor cells, in particular, tumor cells of B cell lineage, such as multiple myeloma cells.

Illustrative ligand-binding domains include antigen binding proteins, such as antigen binding fragments of an antibody, such as scFv, scTCR, extracellular domains of receptors, ligands for cell surface molecules/receptors, or receptor binding domains thereof, and tumor binding proteins. In certain embodiments, the antigen binding domains included in a CAR of the invention can be a variable region (Fv), a CDR, a Fab, an scFv, a VH, a VL, a domain antibody variant (dAb), a camelid antibody (VHH), a fibronectin 3 domain variant, an ankyrin repeat variant and other antigen-specific binding domain derived from other protein scaffolds.

In one embodiment, the binding domain of the CAR is an anti-BCMA single chain antibody (scFv), and may be a murine, human or humanized scFv. Single chain antibodies may be cloned from the V region genes of a hybridoma specific for a desired target. A technique which can be used for cloning the variable region heavy chain (VH) and variable region light chain (VL) has been described, for example, in Orlandi et al., *PNAS,* 1989; 86: 3833-3837. Thus, in certain embodiments, a binding domain comprises an antibody-derived binding domain but can be a non-antibody derived binding domain. An antibody-derived binding domain can be a fragment of an antibody or a genetically engineered product of one or more fragments of the antibody, which fragment is involved in binding with the antigen.

In certain embodiments, the CARs of the present invention may comprise a linker between the various domains, added for appropriate spacing and conformation of the molecule. For example, in one embodiment, there may be a linker between the binding domain VH or VL which may be between 1-10 amino acids long. In other embodiments, the linker between any of the domains of the chimeric antigen receptor may be between 1-20 or 20 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long. Ranges including the numbers described herein are also included herein, e.g., a linker 10-30 amino acids long.

In certain embodiments, linkers suitable for use in the CAR described herein are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)n, glycine-serine polymers, where n is an integer of at least one, glycine-alanine polymers, alanine-serine polymers, and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a CAR can include linkers that are all or partially flexible, such that the linker can include a flexible linker as well as one or more portions that confer less flexible structure to provide for a desired CAR structure. Specific linkers include $(G4S)_n$ linkers, wherein n=1-3, as shown in SEQ ID NOs: 95-97, as well as the linker shown in SEQ ID NO: 96.

The binding domain of the CAR may be followed by a "spacer," or, "hinge," which refers to the region that moves the antigen binding domain away from the effector cell surface to enable proper cell/cell contact, antigen binding and activation (Patel et al., *Gene Therapy*, 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered. In one embodiment, the hinge region comprises a CD8alpha hinge (SEQ ID NO: 97).

The "transmembrane" region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137. In some embodiments, the transmembrane domain comprises the amino acid sequence of SEQ ID NO: 98. In certain embodiments, the transmembrane domain is synthetic in which case it would comprise predominantly hydrophobic residues such as leucine and valine.

The "intracellular signaling domain" or "signaling domain" refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the terms "intracellular signaling domain" or "signaling domain," used interchangeably herein, refer to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRγ chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Cytoplasmic signaling sequences that act in a costimulatory manner may contain signaling motifs which are known as immunoreceptor tyrosine-based activation motif or ITAMs.

Examples of ITAM containing primary cytoplasmic signaling sequences that are of particular use in the invention include those derived from TCRzeta, FcRgamma, FcRbeta, CD3gamma, CD3delta, CD3epsilon, CD5, CD22, CD79a, CD79b and CD66d. In one particular embodiment, the intracellular signaling domain of the anti-BCMA CARs described herein are derived from CD3zeta. In some embodiments, the signaling domain comprises the amino acid sequence of SEQ ID NO: 100.

As used herein, the term, "costimulatory signaling domain," or "costimulatory domain", refers to the portion of the CAR comprising the intracellular domain of a costimulatory molecule. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD3zeta and 4-1BB, other costimulatory domains are contemplated for use with the CARs described herein. The inclusion of one or more co-stimulatory signaling domains may enhance the efficacy and expansion of T cells expressing CAR receptors. The intracellular signaling and costimulatory signaling domains may be linked in any order in tandem to the carboxyl terminus of the transmembrane domain. In some embodiments, the costimulatory domain comprises the amino acid sequence of SEQ ID NO: 99.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant costimulatory signal. Other CARs containing a binding domain, a hinge, a transmembrane and the signaling domain derived from CD3zeta or FcRgamma together with one or more costimulatory signaling domains (e.g., intracellular costimulatory domains derived from CD28, CD137, CD134 and CD278) may more effectively direct antitumor activity as well as increased cytokine secretion, lytic activity, survival and proliferation in CAR expressing T cells in vitro, and in animal models and cancer patients (Milone et al., *Molecular Therapy*, 2009; 17: 1453-1464; Zhong et al., *Molecular Therapy*, 2010; 18: 413-420; Carpenito et al., *PNAS*, 2009; 106:3360-3365).

In various embodiments, the BCMA CARs of the invention comprise (a) an anti-BCMA scFv as a binding domain (e.g., an scFv having binding regions (e.g., CDRs or variable domains) from any one or more of the BCMA antibodies identified in Table 1) (b) a hinge region derived from human CD8alpha, (c) a human CD8alpha transmembrane domain, and (d) a human T cell receptor CD3 zeta chain (CD3) intracellular signaling domain, and optionally one or more costimulatory signaling domains, e.g., 4-1BB. In one embodiment, the different protein domains are arranged from amino to carboxyl terminus in the following order: binding domain, hinge region and transmembrane domain. The intracellular signaling domain and optional co-stimulatory signaling domains are linked to the transmembrane carboxy terminus in any order in tandem to form a single chain chimeric polypeptide. In one embodiment, a nucleic acid construct encoding a BCMA CAR is a chimeric nucleic acid molecule comprising a nucleic acid molecule comprising different coding sequences, for example, (5' to 3') the coding sequences of a human anti-BCMA scFv, a human CD8alpha-hinge, a human CD8alpha transmembrane domain and a CD3zeta intracellular signaling domain. In another embodiment, a nucleic acid construct encoding a BCMA CAR is a chimeric nucleic acid molecule comprising a nucleic acid molecule comprising different coding sequences, for example, (5' to 3') the coding sequences of a human anti-BCMA scFv, a human CD8alpha-hinge, a human CD8alpha transmembrane domain, a 4-1BB co-stimulatory domain, and a CD3zeta co-stimulatory domain.

In certain embodiments, the polynucleotide encoding the CAR described herein is inserted into a vector. The vector is a vehicle into which a polynucleotide encoding a protein may be covalently inserted so as to bring about the expression of that protein and/or the cloning of the polynucleotide. Such vectors may also be referred to as "expression vectors". The isolated polynucleotide may be inserted into a vector using any suitable methods known in the art, for example, without limitation, the vector may be digested using appropriate restriction enzymes and then may be ligated with the isolated polynucleotide having matching restriction ends. Expression vectors have the ability to incorporate and express heterologous or modified nucleic acid sequences coding for at least part of a gene product capable of being transcribed in a cell. In most cases, RNA molecules are then translated into a protein. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra. An expression vector may comprise additional elements, for example, the expression vector may have two replication systems, thus allowing it to be maintained in two organisms, for example in human cells for expression and in a prokaryotic host for cloning and amplification.

The expression vector may have the necessary 5' upstream and 3' downstream regulatory elements such as promoter sequences such as CMV, PGK and EF1alpha. promoters, ribosome recognition and binding TATA box, and 3' UTR AAUAAA transcription termination sequence for the efficient gene transcription and translation in its respective host cell. Other suitable promoters include the constitutive promoter of simian virus 40 (SV40) early promoter, mouse mammary tumor virus (MMTV), HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing chimeric antigen receptor. This provides a molecular switch capable of turning on expression of the polynucleotide sequence of interest or turning off expression. Examples of inducible promoters include, but are not limited to a metallothionine promoter, a glucocorticoid promoter, a progesterone promoter, or a tetracycline promoter.

The expression vector may have additional sequence such as 6×-histidine, c-Myc, and FLAG tags which are incorporated into the expressed CARs. Thus, the expression vector may be engineered to contain 5' and 3' untranslated regulatory sequences that sometimes can function as enhancer sequences, promoter regions and/or terminator sequences that can facilitate or enhance efficient transcription of the nucleic acid(s) of interest carried on the expression vector. An expression vector may also be engineered for replication and/or expression functionality (e.g., transcription and translation) in a particular cell type, cell location, or tissue type. Expression vectors may include a selectable marker for maintenance of the vector in the host or recipient cell.

In various embodiments, the vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are Lenti-X™ Bicistronic Expression System (Neo) vectors (Clontrch), pClneo vectors (Promega) for expression in mammalian cells; pLenti4/V5-DEST™, pLenti6/V5-DEST™, and pLenti6.2N5-GW/lacZ (Invitrogen) for lentivirus-mediated gene transfer and expression in mammalian cells. The coding sequences of the CARs disclosed herein can be ligated into such expression vectors for the expression of the chimeric protein in mammalian cells.

In certain embodiments, the nucleic acids encoding the CAR of the present invention are provided in a viral vector. A viral vector can be that derived from retrovirus, lentivirus, or foamy virus. As used herein, the term, "viral vector," refers to a nucleic acid vector construct that includes at least one element of viral origin and has the capacity to be packaged into a viral vector particle. The viral vector can contain the coding sequence for the various chimeric proteins described herein in place of nonessential viral genes. The vector and/or particle can be utilized for the purpose of transferring DNA, RNA or other nucleic acids into cells either in vitro or in vivo. Numerous forms of viral vectors are known in the art.

In certain embodiments, the viral vector containing the coding sequence for a CAR described herein is a retroviral vector or a lentiviral vector. The term "retroviral vector" refers to a vector containing structural and functional genetic elements that are primarily derived from a retrovirus. The term "lentiviral vector" refers to a vector containing structural and functional genetic elements outside the LTRs that are primarily derived from a lentivirus.

The retroviral vectors for use herein can be derived from any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). Retroviruses" of the invention also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (FIV), equine immnodeficiency virus (EIV), and other classes of retroviruses.

A lentiviral vector for use herein refers to a vector derived from a lentivirus, a group (or genus) of retroviruses that give rise to slowly developing disease. Viruses included within this group include HIV (human immunodeficiency virus; including HIV type 1, and HIV type 2); visna-maedi; a caprine arthritis-encephalitis virus; equine infectious anemia virus; feline immunodeficiency virus (FIV); bovine immune deficiency virus (BIV); and simian immunodeficiency virus (SIV). Preparation of the recombinant lentivirus can be achieved using the methods according to Dull et al. and Zufferey et al. (Dull et al., *J. Virol.*, 1998; 72: 8463-8471 and Zufferey et al., *J. Virol.* 1998; 72:9873-9880).

Retroviral vectors (i.e., both lentiviral and non-lentiviral) for use in the present invention can be formed using standard cloning techniques by combining the desired DNA sequences in the order and orientation described herein (Current Protocols in Molecular Biology, Ausubel, F. M. et al. (eds.) Greene Publishing Associates, (1989), Sections 9.10-9.14 and other standard laboratory manuals; Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Suitable sources for obtaining retroviral (i.e., both lentiviral and non-lentiviral) sequences for use in forming the vectors include, for example, genomic RNA and cDNAs available from commercially available sources, including the Type Culture Collection (ATCC), Rockville, Md. The sequences also can be synthesized chemically.

For expression of a BCMA CAR, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art, as described above. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vectors provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

The CARs of the present invention are introduced into a host cell using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding a BCMA CAR carried by a retroviral vector can be transduced into a cell through infection and pro virus integration.

As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably.

In particular, the CAR of the present invention is introduced and expressed in immune effector cells so as to redirect their specificity to a target antigen of interest, e.g., a malignant plasma cell, e.g. multiple myeloma.

The present invention provides methods for making the immune effector cells which express the CAR as described herein. In one embodiment, the method comprises transfecting or transducing immune effector cells isolated from a subject, such as a subject having a BCMA expressing tumor cell, such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before or after being genetically modified (i.e., transduced or transfected to express a CAR as described herein).

Prior to in vitro manipulation or genetic modification of the immune effector cells described herein, the source of cells may be obtained from a subject. In particular, the immune effector cells for use with the CARs as described herein comprise T cells. T cells can be obtained from a number of sources, including peripheral blood mononuclear cells, bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the invention, the cells are washed with PBS. In an alternative embodiment, the washed solution lacks calcium, and may lack magnesium or may lack many, if not all, divalent cations. As would be appreciated by those of ordinary skill in the art, a washing step may be accomplished by methods known to those in the art, such as by using a semiautomated flowthrough centrifuge. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD1 b, CD16, HLA-DR, and CD8. Flow cytometry and cell sorting may also be used to isolate cell populations of interest for use in the present invention.

PBMCs may be used directly for genetic modification with the CARs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells. In embodiments, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD127, and positive for granzyme B and perforin. In some embodiments, naive CD8+T lymphocytes are characterized by the expression of phenotypic markers of naive T cells including CD62L, CCR7, CD28, CD3, CD 127, and CD45RA.

In certain embodiments, CD4+ T cells are further sorted into subpopulations. For example, CD4+T helper cells can be sorted into naive, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+CD4+ T cell. In some embodiments, central memory CD4+ cells are CD62L positive and CD45RO positive. In some embodiments, effector CD4+ cells are CD62L and CD45RO negative.

The immune effector cells, such as T cells, can be genetically modified following isolation using known methods, or the immune effector cells can be activated and expanded (or differentiated in the case of progenitors) in vitro prior to being genetically modified. In another embodiment, the immune effector cells, such as T cells, are genetically modified with the chimeric antigen receptors described herein (e.g., transduced with a viral vector comprising a nucleic acid encoding a CAR) and then are activated and expanded in vitro. Methods for activating and expanding T cells are known in the art and are described, for example, in U.S. Pat. Nos. 6,905,874; 6,867,041; 6,797,514; WO2012079000. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040,177; 5,827,642; and WO2012129514.

The invention provides a population of modified immune effector cells for the treatment of a patient having a malignancy caused by a BCMA expressing tumor, e.g., multiple myeloma, the modified immune effector cells comprising a BCMA CAR as disclosed herein.

CAR-expressing immune effector cells prepared as described herein can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective amount of cells in the composition is at least 2 cells (for example, at least 1 CD8+ central memory T cell and at least 1 CD4+ helper T cell subset) or is more typically greater than $10^2$ cells, and up to $10^6$ up to and including $10^8$ or $10^9$ cells and can be more than $10^{10}$ cells. The number of cells will depend upon the ultimate use for which the composition is intended as will the type of cells included therein.

The cells may be autologous or heterologous to the patient undergoing therapy. If desired, the treatment may also include administration of mitogens (e.g., PHA) or lymphokines, cytokines, and/or chemokines (e.g., IFN-γ, IL-2, IL-12, TNF-α, IL-18, and TNF-β, GM-CSF, IL-4, IL-13, Flt3-L, RANTES, MIP1α, etc.) as described herein to enhance induction of the immune response.

The CAR expressing immune effector cell populations of the present invention may be administered either alone, or as a pharmaceutical composition in combination with diluents and/or with other components such as IL-2 or other cytokines or cell populations. Briefly, pharmaceutical compositions of the present invention may comprise a CAR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

The anti-tumor immune response induced in a subject by administering CAR expressing T cells described herein using the methods described herein, or other methods known in the art, may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, N.Y., N.Y.

Thus, the present invention provides for methods of treating an individual diagnosed with or suspected of having, or at risk of developing a hematopoietic malignancy characterized in part by the abnormal accumulation of immunoglobulin-producing plasma cells in the bone marrow, such as in multiple myeloma, comprising administering to the individual a therapeutically effective amount of the CAR-expressing immune effector cells as described herein.

In one embodiment, the invention provides a method of treating a subject diagnosed with a BCMA-expressing cancer comprising removing immune effector cells from a subject diagnosed with a BCMA-expressing cancer, genetically modifying said immune effector cells with a vector comprising a nucleic acid encoding a chimeric antigen receptor of the instant invention, thereby producing a population of modified immune effector cells, and administering the population of modified immune effector cells to the same subject. In one embodiment, the immune effector cells comprise T cells.

The methods for administering the cell compositions described herein includes any method which is effective to result in reintroduction of ex vivo genetically modified immune effector cells that either directly express a CAR of the invention in the subject or on reintroduction of the genetically modified progenitors of immune effector cells that on introduction into a subject differentiate into mature immune effector cells that express the CAR. One method comprises transducing peripheral blood T cells ex vivo with a nucleic acid construct in accordance with the invention and returning the transduced cells into the subject.

Binding Properties of the Chimeric Antigen Receptors and Corresponding Antibodies As used herein, the term "binding" in the context of the binding of a chimeric antigen receptor or a corresponding antibody to either, e.g., a predetermined antigen, such as a cell surface protein or fragment thereof, typically refers to an interaction or association between a minimum of two entities or molecular structures, such as an antigen-binding domain:antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody or chimeric antigen receptor as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, *J Immunol Methods*. 1997, 201(2):223-31; Geuijen, C A, et al. *J Immunol Methods*. 2005, 302(1-2): 68-77).

Accordingly, a chimeric antigen receptor or corresponding antibody of the invention binds to the predetermined antigen or cell surface molecule (receptor) having an affinity corresponding to a $K_D$ value that is at least ten-fold lower than its affinity for binding to a non-specific antigen (e.g., BSA, casein). According to the present invention, the affinity of a chimeric antigen receptor or a corresponding antibody with a $K_D$ value that is equal to or less than ten-fold lower than a non-specific antigen may be considered non-detectable binding.

The term "$K_D$" (M) refers to the dissociation equilibrium constant of a particular antigen-binding domain:antigen interaction, or the dissociation equilibrium constant of a corresponding antibody to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g., a chimeric antigen receptor or a corresponding antibody) to its interactive partner molecule (e.g. antigen X) compared to the binding affinity of the molecule (e.g., chimeric antigen receptor or corresponding antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec−1 or 1/s) refers to the dissociation rate constant of a particular antigen-binding domain:antigen interaction, or the dissociation rate constant of a chimeric antigen receptor or a corresponding antibody. Said value is also referred to as the $k_{off}$ value.

The term "$k_a$" (M−1×sec−1 or 1/M) refers to the association rate constant of a particular antigen-binding domain:antigen interaction, or the association rate constant of a chimeric antigen receptor or a corresponding antibody.

The term "$K_A$" (M−1 or 1/M) refers to the association equilibrium constant of a particular antigen-binding domain:antigen interaction, or the association equilibrium constant of a chimeric antigen receptor or a corresponding antibody. The association equilibrium constant is obtained by dividing the $k_a$ by the $k_d$.

The term "EC50" or "$EC_{50}$" refers to the half maximal effective concentration, which includes the concentration of a chimeric antigen receptor that induces a response halfway between the baseline and maximum after a specified exposure time. The $EC_{50}$ essentially represents the concentration of a chimeric antigen receptor where 50% of its maximal effect is observed. In certain embodiments, the $EC_{50}$ value equals the concentration of a chimeric antigen receptor or a corresponding antibody of the invention that gives half-maximal binding to cells expressing an antigen (e.g., a tumor-associated antigen, such as BCMA), as determined by e.g. a FACS binding assay. Thus, reduced or weaker binding is observed with an increased $EC_{50}$, or half maximal effective concentration value.

In one embodiment, decreased binding can be defined as an increased $EC_{50}$ chimeric antigen receptor or corresponding antibody concentration that enables binding to the half-maximal amount of target cells.

Sequence Variants of the Chimeric Antigen Receptors

The chimeric antigen receptors or the present invention may comprise one or more amino acid substitutions, insertions and/or deletions in the framework and/or CDR regions of the heavy and light chain variable domains as compared to the corresponding germline sequences from which the individual antigen-binding domains of the corresponding antibodies were derived. Such mutations can be readily ascertained by comparing the amino acid sequences disclosed herein to germline sequences available from, for example, public antibody sequence databases. The chimeric antigen receptors of the present invention may comprise antigen-binding domains which are derived from any of the exemplary CDR or variable region amino acid sequences disclosed herein, wherein one or more amino acids within one or more framework and/or CDR regions are mutated to the corresponding residue(s) of the germline sequence from which the corresponding antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies that comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence.

Biological Characteristics of the Chimeric Antigen Receptors and Corresponding Antibodies The present invention includes chimeric antigen receptors with antigen-binding domains derived from antibodies that bind human BCMA with high affinity (e.g., nanomolar or sub-nanomolar $K_D$ values).

According to certain embodiments, the present invention includes chimeric antigen receptors with antigen-binding domains derived from corresponding antibodies that bind human BCMA (e.g., at 25° C.) with a $K_D$ of less than about 5 nM as measured by surface plasmon resonance. In certain embodiments, the corresponding antibodies bind BCMA with a $K_D$ of less than about 20 nM, less than about 10 nM, less than about 8 nM, less than about 7 nM, less than about 6 nM, less than about 5 nM, less than about 4 nM, less than about 3 nM, less than about 2 nM, less than about 1 nM, less than about 800 pM, less than about 700 pM, less than about 500 pM, less than about 400 pM, less than about 300 pM, less than about 200 pM, less than about 100 pM, less than about 50 pM, or less than about 25 pM as measured by surface plasmon resonance.

The present invention also includes chimeric antigen receptors with antigen-binding domains derived from corresponding antibodies that bind BCMA with a dissociative half-life (t %) of greater than about 10 minutes or greater than about 125 minutes as measured by surface plasmon resonance at 25° C. In certain embodiments, the corresponding antibodies bind BCMA with a t % of greater than about 3 minutes, greater than about 4 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 110 minutes, or greater than about 120 minutes, as measured by surface plasmon resonance at 25° C.

The present invention also includes chimeric antigen receptors with antigen-binding domains derived from corresponding antibodies that bind specifically to human cell lines which express endogenous BCMA (e.g., NCI-H929, MOLP-8 or OMP-2), as determined by a FACS binding assay.

The present invention also includes engineered cells expressing BCMA-specific chimeric antigen receptors that (i) are activated by BCMA-expressing cells, and/or (ii) exhibit inhibition of tumor growth in immunocompromised mice bearing human multiple myeloma xenografts.

Preparation of Antigen-Binding Domains

The antigen-binding domains of the chimeric antigen receptors of the present invention, which are specific for particular antigens (e.g., BCMA), can be prepared by any antibody generating technology known in the art. In certain embodiments, one or more of the individual components (e.g., heavy and light chains) of the corresponding antibodies of the invention are derived from chimeric, humanized or fully human antibodies. Methods for making such antibodies are well known in the art. For example, one or more of the heavy and/or light chains can be prepared using VELOCIMMUNE™ technology. Using VELOCIMMUNE™ technology (or any other human antibody generating technology), high affinity chimeric antibodies to a particular antigen (e.g., BCMA) are initially isolated having a human variable region and a mouse constant region. The antibodies are characterized and selected for desirable characteristics, including affinity, selectivity, epitope, etc. As discussed herein, these human variable regions (or CDRs) can then be incorporated into the antigen-binding domains of the chimeric antigen receptors.

Polynucleotides and Vectors

The present invention also relates to polynucleotides and vectors encoding the chimeric antigen receptors discussed herein.

In various embodiments, the polynucleotide may comprise an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell).

In various embodiments, the polynucleotides and/or vectors comprise a nucleic acid molecule comprising the nucleotide sequence of SEQ ID NO: 81, SEQ ID NO: 83, SEQ ID NO: 85, SEQ ID NO: 87 or SEQ ID NO: 89. In various embodiments, the polynucleotides and/or vectors comprise a nucleotide sequence encoding the amino acid sequence of SEQ ID NO: 82, SEQ ID NO: 84, SEQ ID NO: 86, SEQ ID NO: 88, or SEQ ID NO: 90. In various embodiments, the polynucleotides and/or vectors comprise a nucleotide sequence encoding the amino acid sequence of SEQ ID NO: 97, SEQ ID NO: 98, SEQ ID NO: 99 or SEQ ID NO: 100.

Methods of Engineering Immune Cells Expressing Chimeric Antigen Receptors

The present invention encompasses methods of preparing immune cells for immunotherapy comprising introducing, ex vivo, into such immune cells the polynucleotides or vectors encoding one of the BCMA-specific chimeric antigen receptors described herein.

The present invention also encompasses immune cells comprising a polynucleotide or lentiviral vector encoding one of the BCMA-specific chimeric antigen receptors discussed herein. In some embodiments, these immune cells are used for immunotherapy (e.g., treatment of cancer).

The present invention also encompasses methods of genetically modifying immune cells to make them more suitable for allogeneic transplantation. According to a first aspect, the immune cell can be made allogeneic, for instance, by inactivating at least one gene expressing one or more component of T-cell receptor (TCR) as described in WO 2013/176915, which can be combined with the inactivation of a gene encoding or regulating HLA or β2m protein expression. Accordingly the risk of graft versus host syndrome and graft rejection is significantly reduced. According to further aspect of the invention, the immune cells can be further manipulated to make them more active or limit exhaustion, by inactivating genes encoding proteins that act as "immune checkpoints" that act as regulators of T-cells activation, such as PD1 or CTLA-4.

Engineered Immune Cells

Immune cells comprising a chimeric antigen receptor of the invention (or engineered immune cells) are another object of the present invention. In some cases, the immune cell is an immune effector cell. In some cases, the immune cell is a T cell. In some cases, the immune cell is a T lymphocyte selected from an inflammatory T lymphocyte, a cytotoxic T lymphocyte, a regulatory T lymphocyte, or a helper T lymphocyte. In some cases, the immune cell is a CD8+ cytotoxic T lymphocyte.

In some embodiments, the engineered immune cell is a human T cell comprising a chimeric antigen receptor comprising, from N-terminus to C-terminus: (a) an extracellular ligand-binding domain comprising an anti-BCMA single chain variable fragment (scFv) domain comprising a light chain variable region (LCVR) and a heavy chain variable region (HCVR); (b) a hinge; (c) a transmembrane domain; and (d) a cytoplasmic domain comprising a costimulatory domain and a signaling domain.

In some embodiments, the scFv domain of the engineered human T cell comprises a LCVR/HCVR amino acid sequence pair comprising the amino acid sequences of SEQ ID NOs: 10/2, 26/18, 42/34, 58/50, or 74/66. In some cases, the hinge comprises the amino acid sequence of SEQ ID NO: 97. In some cases, the transmembrane domain comprises the amino acid sequence of SEQ ID NO: 98. In some cases, the costimulatory domain is a 4-1BB costimulatory domain. In some cases, the 4-1BB costimulatory domain comprises the amino acid sequence of SEQ ID NO: 99. In some cases, the signaling domain is a CD3zeta signaling domain. In some cases, the CD3zeta signaling domain comprises the amino acid sequence of SEQ ID NO: 100.

In various embodiments, the engineered human T cell comprises a chimeric antigen receptor comprising the amino acid sequence of SEQ ID NO: 82, SEQ ID NO: 84, SEQ ID NO: 86, SEQ ID NO: 88, or SEQ ID NO: 90.

Bioequivalents

The present invention encompasses chimeric antigen receptors and engineered cells expressing the chimeric antigen receptors, which have amino acid sequences that vary from those of the exemplary molecules disclosed herein but that retain the ability to bind BCMA, activate immune cells expressing the chimeric antigen receptors in the presence of BCMA-expressing cells, or suppress growth or proliferation of BCMA-expressing tumor cells. Such variant molecules may comprise one or more additions, deletions, or substitutions of amino acids when compared to parent sequence, but exhibit biological activity that is essentially equivalent to that of the described bispecific antigen-binding molecules.

In one embodiment, two engineered immune cells expressing a chimeric antigen receptor of the present invention are bioequivalent if there are no clinically meaningful differences in their safety, purity, and potency.

In one embodiment, two engineered immune cells are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two engineered immune cells are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the engineered cell is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the engineered cell (or its target) is measured as a function of time; and (d) in a well-controlled clinical trial that establishes safety, efficacy, or bioavailability or bioequivalence of an engineered cell.

Bioequivalent variants of the exemplary engineered cells set forth herein may be constructed by, for example, making various substitutions of residues or sequences or deleting terminal or internal residues or sequences not needed for biological activity.

Species Selectivity and Species Cross-Reactivity

According to certain embodiments of the invention, antigen-binding domains are provided which bind to human BCMA, but not to BCMA from other species. The present invention also includes antigen-binding domains that bind to human BCMA and to BCMA from one or more non-human species.

According to certain exemplary embodiments of the invention, antigen-binding domains are provided which bind to human BCMA and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee BCMA.

Activation and Expansion of Engineered Immune Cells

Whether prior to or after genetic modification of the engineered cells (e.g., T cells), even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a costimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, IL-10, IL-2, 1L-15, TGFp, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $O_2$). T cells that have been exposed to varied stimulation times may exhibit different characteristics.

In another particular embodiment, said cells can be expanded by co-culturing with tissue or cells. Said cells can also be expanded in vivo, for example in the subject's blood after administrating said cell into the subject.

Therapeutic Applications

The present invention includes compositions comprising an engineered cell (e.g., a T cell) expressing a chimeric antigen receptor of the invention and a pharmaceutically acceptable vehicle. In some cases, the engineered cells form a medicament, particularly for immunotherapy. In some cases, the engineered cells are used for the treatment of cancer (e.g., multiple myeloma). In some cases, the engineered cells are used in the manufacture of a medicament for immunotherapy and/or the treatment of a cancer (e.g., a BCMA-expressing cancer).

The present invention includes methods comprising administering to a subject in need thereof a therapeutic composition comprising an engineered cell (e.g., a T cell) expressing a chimeric antigen receptor as discussed herein. The therapeutic composition can comprise a cell expressing any chimeric antigen receptor as disclosed herein and a pharmaceutically acceptable carrier, diluent or vehicle. As used herein, the expression "a subject in need thereof" means a human or non-human animal that exhibits one or more symptoms or indicia of cancer (e.g., a subject expressing a tumor or suffering from any of the cancers mentioned herein), or who otherwise would benefit from an inhibition or reduction in BCMA activity or a depletion of BCMA+ cells (e.g., multiple myeloma cells).

The engineered cells of the present invention are useful, inter alia, for treating any disease or disorder in which stimulation, activation and/or targeting of an immune response would be beneficial. In particular, the engineered cells of the present invention may be used for the treatment, prevention and/or amelioration of any disease or disorder associated with or mediated by BCMA expression or activity or the proliferation of BCMA+ cells. Cells expressing BCMA which can be inhibited or killed using the engineered cells of the invention include, for example, multiple myeloma cells.

The engineered cells of the present invention may be used to treat a disease or disorder associated with BCMA expression including, e.g., a cancer including multiple myeloma or other B-cell or plasma cell cancers, such as Waldenström's macroglobulinemia, Burkitt lymphoma, and diffuse large B-Cell lymphoma. In some embodiments, the BCMA-expressing disease or disorder is Castleman disease, lymphoplasmacytic lymphoma, follicular lymphoma, mantle cell lymphoma, marginal zone lymphoma, Hodgkin's lymphoma, Non-Hodgkin's lymphoma, or chronic lymphocytic leukemia. According to certain embodiments of the present invention, the engineered cells are useful for treating a patient afflicted with multiple myeloma. According to other related embodiments of the invention, methods are provided comprising administering an engineered cell as disclosed herein to a patient who is afflicted with multiple myeloma. Analytic/diagnostic methods known in the art, such as tumor scanning, etc., may be used to ascertain whether a patient harbors multiple myeloma or another B-cell lineage cancer.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with BCMA expression (e.g., multiple myeloma) comprising administering a population of engineered cells described elsewhere herein to a subject after the subject has been determined to have multiple myeloma. For example, the present invention includes methods for treating multiple myeloma comprising administering engineered immune cells to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received other immunotherapy or chemotherapy.

The treatments discussed herein can be ameliorating, curative or prophylactic. Treatments may be either part of an autologous immunotherapy or part of an allogeneic immunotherapy. By autologous, it is meant that the cells, cell line or population of cells used for treating patients are originating from the patient or from a Human Leucocyte Antigen (HLA) compatible donor. By allogeneic is meant that the cells, cell line or population of cells used for treating patients are not originating from the patient but from a donor.

Cells that can be used with the disclosed methods are described herein. The treatments can be used to treat patients diagnosed with a pre-malignant or malignant cancer condition characterized by BCMA-expressing cells, especially by an overabundance of BCMA-expressing cells. Such conditions are found in cancers, such as multiple myeloma.

Types of cancers to be treated with the engineered cells of the invention include, but are not limited to multiple myeloma, Waldenström's macroglobulinemia, Burkitt lymphoma, and diffuse large B-Cell lymphoma, as well as other B cell or plasma cell cancers. In some embodiments, the engineered cells can be used to treat a BCMA-expressing disease or disorder, such as Castleman disease, lymphoplasmacytic lymphoma, follicular lymphoma, mantle cell lymphoma, marginal zone lymphoma, Hodgkin's lymphoma, Non-Hodgkin's lymphoma, or chronic lymphocytic leukemia.

Compositions and methods of the present invention may be used to treat a subject who has been characterized as having cells or tissues expressing BCMA, or is suspected of having cells or tissues expressing BCMA. For example, subjects benefiting from treatment according to the invention include subjects with multiple myeloma.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administered in one or more doses. In some embodiments, the effective amount of cells is administered as a single dose. In some embodiments, the effective amount of cells is administered as more than one dose over a period time. Timing of administration is within the judgment of managing physician and depends on the clinical condition of the patient. The cells or population of cells may be obtained from any source, such as a blood bank or a donor. While individual needs vary, determination of ranges of effective amounts of a given cell type for a particular disease or condition are within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In one embodiment, the effective amount of cells or composition comprising those cells is administered parenterally. This administration can be an intravenous administration. In some cases, administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation.

In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. In certain embodiments, any means (e.g., surgery, chemotherapy, or radiation therapy) may be used to reduce the tumor burden prior to administration of the expanded immune cells of the invention. In one embodiment, reducing the tumor burden prior to administration of the engineered cells of the invention can reduce the potential for, or prevent, cytokine release syndrome or a cytokine storm, a side effect that may be associated with CAR T cell therapy.

Combination Therapies

The present invention provides methods which comprise administering engineered cells or a population of cells comprising any of the chimeric antigen receptors described herein in combination with one or more additional therapeutic agents. Exemplary additional therapeutic agents that may be combined with or administered in combination with the cells or population of cells of the present invention include, e.g., an anti-tumor agent (e.g. chemotherapeutic agents including melphalan, vincristine (Oncovin), cyclophosphamide (Cytoxan), etoposide (VP-16), doxorubicin (Adriamycin), liposomal doxorubicin (Doxil), obendamustine (Treanda), or any others known to be effective in treating a plasma cell tumor in a subject). In some embodiments, the second therapeutic agent comprises steroids. In some embodiments, the second therapeutic agent comprises targeted therapies including thalidomide, lenalidomide, and bortezomib, which are therapies approved to treat newly diagnosed patients. Lenalidomide, pomalidomide, bortezomib, carfilzomib, panobinostat, ixazomib, elotuzumab, and daratumumab are examples of a second therapeutic agent effective for treating recurrent myeloma. In certain embodiments the second therapeutic agent is a regimen comprising radiotherapy or a stem cell transplant. In certain embodiments, the second therapeutic agent may be an immunomodulatory agent. in certain embodiments, the second therapeutic agent may be a proteasome inhibitor, including bortezomib (Velcade), carfilzomib (Kyprolis), ixazomib (Ninlaro). In certain embodiments the second therapeutic agent may be a histone deacetylase inhibitor such as panobinostat (Farydak). In certain embodiments, the second therapeutic agent may be a monoclonal antibody, an antibody drug conjugate, a bispecific antibody conjugated to an anti-tumor agent, a checkpoint inhibitor, or combinations thereof. Other agents that may be beneficially administered in combination with the antigen-binding molecules of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising engineered cells or populations of cells as disclosed herein) may also be administered as part of a therapeutic regimen comprising one or more therapeutic combinations selected from a monoclonal antibody other than those described herein, which may interact with a different antigen on the plasma cell surface, a bispecific antibody, which has one arm that binds to an antigen on the tumor cell surface and the other arm binds to an antigen on a T cell, an antibody drug conjugate, a bispecific antibody conjugated with an anti-tumor agent, a checkpoint inhibitor, for example, one that targets, PD-1 or CTLA-4, or combinations thereof. In certain embodiments, the checkpoint inhibitors may be selected from PD-1 inhibitors, such as pembrolizumab (Keytruda), nivolumab (Opdivo), or cemiplimab (REGN2810). In certain embodiments, the checkpoint inhibitors may be selected from PD-L1 inhibitors, such as atezolizumab (Tecentriq), avelumab (Bavencio), or Durvalumab (Imfinzi)). In certain embodiments, the checkpoint inhibitors may be selected from CTLA-4 inhibitors, such as ipilimumab (Yervoy).

The present invention also includes therapeutic combinations comprising any of the engineered cells or populations of cells mentioned herein and an inhibitor of one or more of VEGF, Ang2, DLL4, EGFR, ErbB2, ErbB3, ErbB4, EGFRvIII, cMet, IGF1R, B-raf, PDGFR-α, PDGFR-β, FOLH1 (PSMA), PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). In some embodiments, the engineered cells or population of cells of the invention may also be administered as part of a treatment regimen that also includes radiation treatment and/or conventional chemotherapy.

The additional therapeutically active component(s) may be administered just prior to, concurrent with, or shortly after the administration of the engineered cells of the present invention; (for purposes of the present disclosure, such administration regimens are considered the administration of the engineered cells "in combination with" an additional therapeutically active component).

The present invention includes pharmaceutical compositions in which an engineered cell or population of cells of the present invention is co-formulated with one or more of the additional therapeutically active component(s) as described elsewhere herein.

Administration Regimens

According to certain embodiments of the present invention, multiple doses of the engineered cells may be administered to a subject over a defined time course. The methods according to this aspect of the invention comprise sequentially administering to a subject multiple doses of the cells. As used herein, "sequentially administering" means that each dose is administered to the subject at a different point in time, e.g., on different days separated by a predetermined interval (e.g., hours, days, weeks or months). The present invention includes methods which comprise sequentially administering to the patient a single initial dose, followed by one or more secondary doses, and optionally followed by one or more tertiary doses.

The terms "initial dose," "secondary doses," and "tertiary doses," refer to the temporal sequence of administration of the engineered cells of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of engineered cells, but generally may differ from one another in terms of frequency of administration. In certain embodiments, however, the amount of engineered cells contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose which is administered to a patient prior to the administration of the very next dose in the sequence with no intervening doses.

The methods according to this aspect of the invention may comprise administering to a patient any number of secondary and/or tertiary doses. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Anti-BCMA Antibodies

Anti-BCMA antibodies were obtained by immunizing a genetically modified mouse with a human BCMA antigen (e.g., hBCMA, SEQ ID NO: 101), or by immunizing an engineered mouse comprising DNA encoding human immunoglobulin heavy and kappa light chain variable regions with a human BCMA antigen.

Following immunization, splenocytes were harvested from each mouse and either (1) fused with mouse myeloma cells to preserve their viability and form hybridoma cells and screened for BCMA specificity, or (2) B-cell sorted (as described in US 2007/0280945A1) using a human BCMA fragment as the sorting reagent that binds and identifies reactive antibodies (antigen-positive B cells).

Chimeric antibodies to BCMA were initially isolated having a human variable region and a mouse constant region. The antibodies were characterized and selected for desirable characteristics, including affinity, selectivity, etc. If necessary, mouse constant regions were replaced with a desired human constant region, for example wild-type or modified IgG1 or IgG4 constant region, to generate a fully human anti-BCMA antibody. While the constant region selected may vary according to specific use, high affinity antigen-binding and target specificity characteristics reside in the variable region.

Heavy and Light Chain Variable Region Amino Acid and Nucleic Acid Sequences of Anti-BCMA Antibodies:

Table 1 sets forth the amino acid sequence identifiers of the heavy and light chain variable regions and CDRs of selected anti-BCMA antibodies of the invention. The corresponding nucleic acid sequence identifiers are set forth in Table 2.

TABLE 1

| Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| mAb16711 | 2 | 4 | 6 | 8 | 10 | 12 | 14 | 16 |
| mAb16716 | 18 | 20 | 22 | 24 | 26 | 28 | 30 | 32 |
| mAb16732 | 34 | 36 | 38 | 40 | 42 | 44 | 46 | 48 |
| mAb16747 | 50 | 52 | 54 | 56 | 58 | 60 | 62 | 64 |
| mAb21581 | 66 | 68 | 70 | 72 | 74 | 76 | 78 | 80 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb16711 | 1 | 3 | 5 | 7 | 9 | 11 | 13 | 15 |
| mAb16716 | 17 | 19 | 21 | 23 | 25 | 27 | 29 | 31 |
| mAb16732 | 33 | 35 | 37 | 39 | 41 | 43 | 45 | 47 |
| mAb16747 | 49 | 51 | 53 | 55 | 57 | 59 | 61 | 63 |
| mAb21581 | 65 | 67 | 69 | 71 | 73 | 75 | 77 | 79 |

Example 2: Generation of BCMA-Specific Chimeric Antigen Receptors

Six anti-BCMA antibodies (mAb16711, mAb16716, mAb16732, mAb16747, and mAb21581) were reformatted into VL-VH single chain variable fragments (ScFv) and placed into a chimeric antigen receptor (CAR) construct that used a CD8α hinge and transmembrane domain, 4-1BB costimulatory domain, and a CD3ζ stimulatory domain. The BCMA specific CARs were cloned into a lenti-viral expression vector (Lenti-X™ Bicistronic Expression System (Neo), Clontech Cat #632181) and lentiviral particles were generated via the Lenti-X Packaging Single-Shot (VSV-G) system (Clontech Cat #631276) according to manufacturer protocols. Jurkat cells engineered to express an NFAT-luciferase reporter (Jurkat/NFATLuc cl. 3C7) were then transduced with the different CAR constructs using RetroNectin® Precoated Dishes (Clontech, Cat #T110a) according to manufacturer's protocols. Following selection for at least 2 weeks in 500 μg/ml G418 (Gibco, Cat #11811-098), the following CAR-T cell lines were generated; Jurkat/NFATLuc cl. 3C7/BCMA 16716 VL-VH CART, Jurkat/NFATLuc cl. 3C7/BCMA 16711 VL-VH CART, Jurkat/NFATLuc cl. 3C7/BCMA 16732 VL-VH CART, Jurkat/NFATLuc cl. 3C7/BCMA 16747 VL-VH CART, Jurkat/NFATLuc cl. 3C7/BCMA 21581 VL-VH CART. The nucleotide sequences of the CAR constructs used in the generation of these CAR-T cell lines, as illustrated in FIG. 1, are shown in SEQ ID NOs: 81 (mAb16711 VL/VH), 83 (mAb16716 VL/VH), 85 (mAb16732 VL/VH), 87 (mAb16747 VL/VH), and 89 (mAb21581 VL/VH). These six CAR-T cell lines were used to evaluate cell surface expression and activation of BCMA CAR-T cells, as discussed in Example 3.

Chimeric antigen receptors containing an anti-BCMA VL-VH scFv, a huCD8 transmembrane domain, a 4-1BB co-stimulatory domain, and a CD3ζ signaling domain were constructed using the VL and VH nucleotide sequences of two anti-BCMA antibodies, mAb21581 and mAb16747 (corresponding to SEQ ID NOs: 89 and 87, respectively). As a non-binding control, a similar CAR was designed using the nucleotide sequence of an irrelevant scFv (CAR construct of SEQ ID NO: 91). These CARs were cloned into a pLVX lentiviral vector with an EF1a promoter and IRES:eGFP sequence (for tracking CAR-transduced cells) and VSV-pseudotyped lentivirus was produced.

CD3+ T cells were isolated from human peripheral blood mononuclear cells (PBMCs), stimulated with CD3/CD28 microbeads plus 100 U/ml recombinant human IL-2, and transduced with the lentivirus at an MOI=5. The transduced cells were expanded for 3 weeks with CD3/CD28 microbeads plus 100 U/ml recombinant human IL-2 before being cryopreserved until use during the in vivo experiment. These three lines of CAR-T cells were used to evaluate efficacy in the reduction of tumor burden in vivo, as discussed in Examples 4 and 5.

Example 3: Cell Surface Expression of BCMA CAR Constructs in Jurkat Cells and Activation of BCMA CAR-T Cells Relative cell surface expression of the BCMA CAR constructs in Jurkat/NFATLuc cells was accessed by flow cytometry. To stain, cells were plated in staining buffer (PBS, without Calcium and Magnesium (Irving 9240)+2% FBS (ATCC 30-2020) at a density of 200,000 cells per well in a 96 well V-Bottom plate and stained for 30 mins at 4° C. with 10 ug/ml of the BCMA extracellular domain fused to an hIgG1-Fc (BCMA ecto-hFc) or an irrelevant protein fused to hIgG1-Fc (Fc isotype control). Following incubation with BCMA-hFc or Fc isotype control, cells were washed once in staining buffer, and stained with an Alexa-Flour 647 conjugated secondary antibody (Jackson ImmunoResearch, Cat #109-606-170) at 10 μg/ml for 30 mins at 4° C. Cells were then washed and fixed using a 50% solution of BD Cytofix (BD, Cat #554655) diluted in staining buffer. Samples were run on the Intellicyt iQue flow cytometer and analyzed by FlowJo 10.2 to calculate the mean fluorescent intensity (MFI). The signal to noise ratio (S:N) is determined by taking the ratio of the BCMA-hFc or Fc isotype control MFI to the secondary antibody alone MFI.

Activity of the CAR-T lines was assessed in a CAR-T/APC (Antigen presenting cell) bioassay. To perform the bioassay, 50,000 CAR-T cells were added to Thermo-Nunc 96 well white plates (Thermo Scientific, Cat #136101) in 50 ul of assay media (RPMI media with 10% FBS and 1% P/S/G) followed by the addition of a 3-fold serial dilution of APCs (500,000 cells to 685 cells) in 50 ul of assay media. The following APCs were utilized: RAJI, Daudi, RPMI8226 (endogenously express BCMA), and HEK293 (BCMA negative). The cell mixture was incubated in a 37° C., 5% C02, humidified incubator for 5 hours. NFAT-Luciferase activity was measured using Promega One-Glo (Cat #E6130) and a Perkin Elmer Envision plate reader. Relative luciferase units (RLU) were generated and plotted in GraphPad Prism using a four-parameter logistic equation over an 8-point response curve. The zero APC condition for each dose-response curve is also included in the analysis as a continuation of the three-fold serial dilution and is represented as the lowest dose. CAR-T activity was determined by taking the ratio of the highest RLU on the curve to the lowest and is represented as signal:noise (S:N) in Table 4.

Table 3 shows that the 16747 and 21581 CAR-Ts had similar surface expression with the S:N ranging from 209-273, 16716 CAR-T expressed at 44-fold above background, while 16732 and 16711 CAR expression was much lower with an S:N of 13 and 4, respectively.

Table 4 shows that all six BCMA CAR-T cell lines were activated by RAJI, Daudi and RPMI8226 cells. No CAR-T cell lines were activated by HEK293. The 16747 BCMA CAR had the strongest activation in the CAR-T/APC bioassay while CAR 16711 had the weakest activity regardless of the BCMA expressing APC. Lastly, a correlation between CAR expression (Table 3) and CAR activity (Table 4) was observed.

TABLE 3

Soluble FC-BCMA Binding on BCMA CAR-T Cell Lines

| Cell Line | S:N (BCMA-hFc) | S:N (Isotype-hFc) |
|---|---|---|
| Jurkat/NFATLuc cl. 3C7 | 1.5 | 0.8 |
| Jurkat/NFATLuc cl. 3C7/ 16716 VL-VH CART | 44.0 | 1.1 |
| Jurkat/NFATLuc cl. 3C7/ 16711 VL-VH CART | 3.7 | 1.2 |
| Jurkat/NFATLuc cl. 3C7/ 16732 VL-VH CART | 13.1 | 1.0 |
| Jurkat/NFATLuc cl. 3C7/ 16747 VL-VH CART | 209.2 | 1.3 |
| Jurkat/NFATLuc cl. 3C7/ 21581 VL-VH CART | 224.5 | 1.2 |

TABLE 4

Activation of BCMA CAR-T's in a CAR-T/APC Bioassay

| Antigen Presenting Cell | CAR-T Max Activity | | | | | |
|---|---|---|---|---|---|---|
| | No CAR | 16716 | 16711 | 16732 | 16747 | 21581 |
| RAJI | 1.2 | 16.3 | 7.9 | 16.8 | 38.9 | 26.9 |
| Daudi | 1.0 | 6.4 | 2.6 | 4.9 | 14.0 | 8.0 |
| RPMI8226 | 0.8 | 6.6 | 1.8 | 5.2 | 12.5 | 12.3 |
| HEK293 | 0.9 | 0.8 | 0.9 | 0.8 | 0.9 | 0.9 |

Example 4: BCMA-Targeted CAR-T Cells Reduce Growth of BCMA-Expressing Tumors (OPM-2) In Vivo in a Xenogenic Tumor Model To determine the in vivo efficacy of BCMA-targeted chimeric antigen receptor (CAR) T cells, a xenogenic tumor study was performed in mice using OPM-2 human multiple myeloma cells, which express high levels of BCMA.

Implantation and Measurement of Xenogenic Tumors:

On day 0, immunodeficient NOD.Cg-Prkdc$^{scid}$||2rg$^{tm1Wjl}$/SzJ (NSG) mice were intravenously administered $2\times10^6$ BCMA$^+$ OPM-2 human multiple myeloma tumor cells that were engineered to also express firefly luciferase (OPM-2-luciferase cells). On day 21, the mice were intravenously injected with $2\times10^6$ T cells that express either the control CAR or an anti-BCMA CAR (as determined by the frequency of cells expressing GFP, which is a marker for those cells that have been transduced with CAR). The mice (n=5 per group) were administered $2\times10^6$ irrelevant scFc CAR T (control scFv CAR), $2\times10^6$ anti-BCMA CAR T encoding the 21581 scFv CAR, or $2\times10^6$ anti-BCMA CAR T encoding the 16747 scFv. Tumor growth was assessed through day 61 by measuring tumor bioluminescence (BLI) in anesthetized animals. As a positive control, a group of mice (n=5) was given only OPM-2-luciferase cells, but not T cells. In order to measure background BLI levels, a group of mice (n=5) were untreated and did not receive tumors or T cells.

Measurement of Xenogenic Tumor Growth:

BLI imaging was used to measure tumor burden. Mice were injected IP with 150 mg/kg of the luciferase substrate D-luciferin suspended in PBS. Five minutes after this injection, BLI imaging of the mice was performed under isoflurane anesthesia using the Xenogen IVIS system. Image acquisition was carried out with the field of view at D, subject height of 1.5 cm, and medium binning level with automatic exposure time determined by the Living Image Software. BLI signals were extracted using Living Image software: regions of interest were drawn around each tumor mass and photon intensities were recorded as p/s/cm2/sr.

While the BCMA$^+$ OPM-2-luciferase tumors grew progressively in mice receiving irrelevant scFv CAR T cells, CAR T cells encoding the 21581 scFV CAR reduced tumor burdens to background levels in the majority of animals and CAR T cells encoding the 16747 scFv CAR reduced tumor burdens to background levels in all of the animals. Results are shown in Table 5a, below.

TABLE 5a

Average Tumor Size (by radiance) at Various Time Points

| CAR T Treatment | |
|---|---|
| | Radiance [p/s/cm2$^2$/sr] 5 days post-implantation (mean ± SEM) |
| No tumor (background BLI) | 6.22E+05 ± 2.77E+04 |
| No CAR T (positive control) | 5.62E+05 ± 2.75E+04 |
| Control CAR T (Irrelevant scFv) $2 \times 10^6$ cells | 5.95E+05 ± 2.40E+04 |
| Anti-BCMA CAR (21581 scFv) $2 \times 10^6$ cells | 6.07E+05 ± 3.97E+04 |
| Anti-BCMA CAR (16747 scFv) $2 \times 10^6$ cells | 5.54E+05 ± 2.80E+04 |
| | Radiance [p/s/cm2$^2$/sr] 11 days post-implantation (mean ± SEM) |
| No tumor (background BLI) | 6.90E+05 ± 3.64E+04 |
| No CAR T (positive control) | 6.22E+05 ± 3.34E+04 |
| Control CAR T (Irrelevant scFv) $2 \times 10^6$ cells | 6.80E+05 ± 2.76E+04 |
| Anti-BCMA CAR (21581 scFv) $2 \times 10^6$ cells | 7.13E+05 ± 2.90E+04 |
| Anti-BCMA CAR (16747 scFv) $2 \times 10^6$ cells | 6.30E+05 ± 2.42E+04 |
| | Radiance [p/s/cm2$^2$/sr] 20 days post-implantation (mean ± SEM) |
| No tumor (background BLI) | 7.59E+05 ± 5.82E+04 |
| No CAR T (positive control) | 2.32E+06 ± 2.94E+05 |
| Control CAR T (Irrelevant scFv) $2 \times 10^6$ cells | 2.80E+06 ± 5.26E+05 |
| Anti-BCMA CAR (21581 scFv) $2 \times 10^6$ cells | 3.06E+06 ± 4.42E+05 |
| Anti-BCMA CAR (16747 scFv) $2 \times 10^6$ cells | 2.53E+06 ± 2.22E+05 |
| | Radiance [p/s/cm2$^2$/sr] 26 days post-implantation (mean ± SEM) |
| No tumor (background BLI) | 5.51E+05 ± 2.51E+04 |
| No CAR T (positive control) | 5.96E+06 ± 8.74E+05 |
| Control CAR T (Irrelevant scFv) $2 \times 10^6$ cells | 8.03E+06 ± 1.41E+06 |
| Anti-BCMA CAR (21581 scFv) $2 \times 10^6$ cells | 6.76E+06 ± 1.34E+06 |
| Anti-BCMA CAR (16747 scFv) $2 \times 10^6$ cells | 6.96E+06 ± 3.39E+05 |
| | Radiance [p/s/cm2$^2$/sr] 31 days post-implantation (mean ± SEM) |
| No tumor (background BLI) | 6.62E+05 ± 3.35E+04 |
| No CAR T (positive control) | 1.58E+07 ± 4.84E+06 |
| Control CAR T (Irrelevant scFv) $2 \times 10^6$ cells | 1.57E+07 ± 3.05E+06 |
| Anti-BCMA CAR (21581 scFv) $2 \times 10^6$ cells | 1.44E+07 ± 2.12E+06 |
| Anti-BCMA CAR (16747 scFv) $2 \times 10^6$ cells | 1.01E+07 ± 5.46E+05 |

TABLE 5a-continued

Average Tumor Size (by radiance) at Various Time Points

| CAR T Treatment | Radiance [p/s/cm$^2$/sr] 34 days post-implantation (mean ± SEM) |
|---|---|
| No tumor (background BLI) | 4.57E+05 ± 1.04E+04 |
| No CAR T (positive control) | 3.36E+07 ± 1.27E+07 |
| Control CAR T (Irrelevant scFv) 2 × 10$^6$ cells | 3.00E+07 ± 2.82E+06 |
| Anti-BCMA CAR (21581 scFv) 2 × 10$^6$ cells | 2.05E+07 ± 3.56E+06 |
| Anti-BCMA CAR (16747 scFv) 2 × 10$^6$ cells | 8.31E+06 ± 9.79E+05 |
| | Radiance [p/s/cm$^2$/sr] 38 days post-implantation (mean ± SEM) |
| No tumor (background BLI) | 6.60E+05 ± 3.13E+04 |
| No CAR T (positive control) | 3.91E+07 ± 6.87E+06 |
| Control CAR T (Irrelevant scFv) 2 × 10$^6$ cells | 4.25E+07 ± 5.08E+06 |
| Anti-BCMA CAR (21581 scFv) 2 × 10$^6$ cells | 2.19E+07 ± 7.88E+06 |
| Anti-BCMA CAR (16747 scFv) 2 × 10$^6$ cells | 1.90E+06 ± 1.20E+06 |
| | Radiance [p/s/cm$^2$/sr] 40 days post-implantation (mean ± SEM) |
| No tumor (background BLI) | 5.39E+05 ± 9.67E+03 |
| No CAR T (positive control) | Animals Euthanized |
| Control CAR T (Irrelevant scFv) 2 × 10$^6$ cells | Animals Euthanized |
| Anti-BCMA CAR (21581 scFv) 2 × 10$^6$ cells | 1.13E+07 ± 4.84E+06 |
| Anti-BCMA CAR (16747 scFv) 2 × 10$^6$ cells | 8.71E+05 ± 2.80E+05 |
| | Radiance [p/s/cm$^2$/sr] 47 days post-implantation (mean ± SEM) |
| No tumor (background BLI) | 7.73E+05 ± 1.91E+04 |
| No CAR T (positive control) | Animals Euthanized |
| Control CAR T (Irrelevant scFv) 2 × 10$^6$ cells | Animals Euthanized |
| Anti-BCMA CAR (21581 scFv) 2 × 10$^6$ cells | 3.17E+07 ± 3.11E+07 |
| Anti-BCMA CAR (16747 scFv) 2 × 10$^6$ cells | 8.85E+05 ± 3.72E+04 |
| | Radiance [p/s/cm$^2$/sr] 54 days post-implantation (mean ± SEM) |
| No tumor (background BLI) | 7.49E+05 ± 1.95E+04 |
| No CAR T (positive control) | Animals Euthanized |
| Control CAR T (Irrelevant scFv) 2 × 10$^6$ cells | Animals Euthanized |
| Anti-BCMA CAR (21581 scFv) 2 × 10$^6$ cells | 4.34E+07 ± 4.29E+07 |
| Anti-BCMA CAR (16747 scFv) 2 × 10$^6$ cells | 8.24E+05 ± 5.48E+04 |
| | Radiance [p/s/cm$^2$/sr] 61 days post-implantation (mean ± SEM) |
| No tumor (background BLI) | 6.18E+05 ± 2.77E+04 |
| No CAR T (positive control) | Animals Euthanized |
| Control CAR T (Irrelevant scFv) 2 × 10$^6$ cells | Animals Euthanized |
| Anti-BCMA CAR (21581 scFv) 2 × 10$^6$ cells | 6.41E+05 ± 4.07E+04 |
| Anti-BCMA CAR (16747 scFv) 2 × 10$^6$ cells | 5.40E+05 ± 2.93E+04 |

A further experiment was performed as discussed above, except that the mice were intravenously injected with 2×10$^6$ T cells that express either the control CAR or an anti-BCMA CAR on day 22 (rather than day 21), and tumor growth was assessed through day 56 (rather than day 61).

While the BCMA$^+$ OPM-2-luciferase tumors grew progressively in mice receiving irrelevant scFv CAR T cells, CAR T cells encoding the 21581 and 16747 scFV CARs reduced tumor burdens to background levels in all of the animals. Results are shown in Table 5b, below.

TABLE 5b

Average Tumor Size (by radiance) at Various Time Points

| CAR T Treatment | Radiance [p/s/cm$^2$/sr] 14 days post-implantation (mean ± SEM) |
|---|---|
| No tumor (background BLI) | 6.72E+05 ± 1.50E+04 |
| No CAR T (positive control) | 7.93E+05 ± 8.18E+04 |
| Control CAR T (Irrelevant scFv) 2 × 10$^6$ cells | 7.09E+05 ± 2.13E+04 |
| Anti-BCMA CAR (21581N scFv) 2 × 10$^6$ cells | 7.87E+05 ± 1.20E+05 |
| Anti-BCMA CAR (16747P scFv) 2 × 10$^6$ cells | 8.93E+05 ± 9.05E+04 |
| | Radiance [p/s/cm$^2$/sr] 20 days post-implantation (mean ± SEM) |
| No tumor (background BLI) | 5.32E+05 ± 3.64E+04 |
| No CAR T (positive control) | 3.07E+06 ± 3.01E+05 |
| Control CAR T (Irrelevant scFv) 2 × 10$^6$ cells | 2.91E+06 ± 2.46E+05 |
| Anti-BCMA CAR (21581N scFv) 2 × 10$^6$ cells | 2.57E+06 ± 8.27E+05 |
| Anti-BCMA CAR (16747P scFv) 2 × 10$^6$ cells | 3.13E+06 ± 5.97E+05 |
| | Radiance [p/s/cm$^2$/sr] 23 days post-implantation (mean ± SEM) |
| No tumor (background BLI) | 5.56E+05 ± 4.29E+04 |
| No CAR T (positive control) | 1.01E+07 ± 1.28E+06 |
| Control CAR T (Irrelevant scFv) 2 × 10$^6$ cells | 8.37E+06 ± 1.38E+06 |
| Anti-BCMA CAR (21581N scFv) 2 × 10$^6$ cells | 1.00E+07 ± 3.92E+06 |
| Anti-BCMA CAR (16747P scFv) 2 × 10$^6$ cells | 8.26E+06 ± 1.59E+06 |
| | Radiance [p/s/cm$^2$/sr] 27 days post-implantation (mean ± SEM) |
| No tumor (background BLI) | 5.18E+05 ± 2.87E+04 |
| No CAR T (positive control) | 1.67E+07 ± 1.54E+06 |
| Control CAR T (Irrelevant scFv) 2 × 10$^6$ cells | 1.47E+07 ± 2.36E+06 |
| Anti-BCMA CAR (21581N scFv) 2 × 10$^6$ cells | 1.59E+07 ± 6.36E+06 |
| Anti-BCMA CAR (16747P scFv) 2 × 10$^6$ cells | 1.03E+07 ± 1.71E+06 |
| | Radiance [p/s/cm$^2$/sr] 30 days post-implantation (mean ± SEM) |
| No tumor (background BLI) | 5.18E+05 ± 1.29E+04 |
| No CAR T (positive control) | 1.93E+07 ± 3.10E+06 |
| Control CAR T (Irrelevant scFv) 2 × 10$^6$ cells | 2.03E+07 ± 2.48E+06 |
| Anti-BCMA CAR (21581N scFv) 2 × 10$^6$ cells | 7.21E+06 ± 1.97E+06 |
| Anti-BCMA CAR (16747P scFv) 2 × 10$^6$ cells | 1.16E+07 ± 3.61E+06 |
| | Radiance [p/s/cm$^2$/sr] 34 days post-implantation (mean ± SEM) |
| No tumor (background BLI) | 5.66E+05 ± 3.76E+04 |
| No CAR T (positive control) | 3.69E+07 ± 6.27E+06 |
| Control CAR T (Irrelevant scFv) 2 × 10$^6$ cells | 4.07E+07 ± 4.13E+06 |
| Anti-BCMA CAR (21581N scFv) 2 × 10$^6$ cells | 5.74E+05 ± 1.24E+04 |
| Anti-BCMA CAR (16747P scFv) 2 × 10$^6$ cells | 1.66E+06 ± 9.09E+05 |
| | Radiance [p/s/cm$^2$/sr] 38 days post-implantation (mean ± SEM) |
| No tumor (background BLI) | 5.43E+05 ± 3.32E+04 |
| No CAR T (positive control) | Animals Euthanized |
| Control CAR T (Irrelevant scFv) 2 × 10$^6$ cells | 5.87E+07 ± 5.72E+06 |
| Anti-BCMA CAR (21581N scFv) 2 × 10$^6$ cells | 5.39E+05 ± 1.58E+04 |
| Anti-BCMA CAR (16747P scFv) 2 × 10$^6$ cells | 5.55E+05 ± 5.02E+04 |
| | Radiance [p/s/cm$^2$/sr] 44 days post-implantation (mean ± SEM) |
| No tumor (background BLI) | 6.42E+05 ± 3.33E+04 |
| No CAR T (positive control) | Animals Euthanized |
| Control CAR T (Irrelevant scFv) 2 × 10$^6$ cells | Animals Euthanized |
| Anti-BCMA CAR (21581N scFv) 2 × 10$^6$ cells | 6.68E+05 ± 3.09E+04 |
| Anti-BCMA CAR (16747P scFv) 2 × 10$^6$ cells | 5.39E+05 ± 2.25E+04 |

TABLE 5b-continued

Average Tumor Size (by radiance) at Various Time Points

| CAR T Treatment | Radiance [p/s/cm2²/sr] 56 days post-implantation (mean ± SEM) |
|---|---|
| No tumor (background BLI) | 8.10E+05 ± 5.92E+04 |
| No CAR T (positive control) | Animals Euthanized |
| Control CAR T (Irrelevant scFv) 2 × 10⁶ cells | Animals Euthanized |
| Anti-BCMA CAR (21581N scFv) 2 × 10⁶ cells | 6.37E+05 ± 2.71E+04 |
| Anti-BCMA CAR (16747P scFv) 2 × 10⁶ cells | 7.13E+05 ± 4.17E+04 |

Example 5: BCMA-Targeted CAR-T Cells Reduce Growth of BCMA-Expressing Tumors (MOLP-8) In Vivo in a Xenogenic Tumor Model To determine the in vivo efficacy of BCMA-targeted chimeric antigen receptor (CAR) T cells, a xenogenic tumor study was performed in mice using MOLP-8 human multiple myeloma cells, which express low levels of BCMA.

Implantation and measurement of xenogenic tumors: On day 0, immunodeficient NOD.Cg-Prkdc$^{scid}$||2rg$^{tm1Wjt}$/SzJ (NSG) mice were intravenously administered 2×10⁶ BCMA⁺ MOLP-8 human multiple myeloma tumor cells that were engineered to also express firefly luciferase (MOLP-8-luciferase cells). On day 12, the mice were intravenously injected with 2×10⁶ T cells that express either the control CAR or an anti-BCMA CAR (as determined by the frequency of cells expressing GFP, which is a marker for those cells that have been transduced with CAR). The mice (n=5 per group) were administered 2×10⁶ irrelevant scFv CAR T (control scFv CAR), 2×10⁶ anti-BCMA CAR T encoding the 21581 scFv CAR, or 2×10⁶ anti-BCMA CAR T encoding the 16747 scFv. Tumor growth was assessed throughout the experiment by measuring tumor bioluminescence (BLI) in anesthetized animals. As a positive control, a group of mice (n=5) was given only MOLP-8-luciferase cells, but not T cells. In order to measure background BLI levels, a group of mice (n=5) were untreated and did not receive tumors or T cells.

Measurement of xenogenic tumor growth: BLI imaging was used to measure tumor burden. Mice were injected IP with 150 mg/kg of the luciferase substrate D-luciferin suspended in PBS. Five minutes after this injection, BLI imaging of the mice was performed under isoflurane anesthesia using the Xenogen IVIS system. Image acquisition was carried out with the field of view at D, subject height of 1.5 cm, and medium binning level with automatic exposure time determined by the Living Image Software. BLI signals were extracted using Living Image software: regions of interest were drawn around each tumor mass and photon intensities were recorded as p/s/cm2/sr.

While the BCMA⁺ MOLP-8-luciferase tumors grew progressively in mice receiving irrelevant scFv CAR T cells, CAR T cells encoding the 21581 scFV CAR and the 16747 scFv CAR reduced tumor burdens to background levels in all of the animals. Results are shown in Table 6, below.

TABLE 6

Average Tumor Size (by radiance) at Various Time Points

| CAR T Treatment | Radiance [p/s/cm2²/sr] 12 days post-implantation (mean ± SEM) |
|---|---|
| No tumor (background BLI) | 6.81E+05 ± 3.46E+04 |
| No CAR T (positive control) | 1.51E+06 ± 7.81E+04 |
| Control CAR T (Irrelevant scFv) 2 × 10⁶ cells | 1.72E+06 ± 1.33E+05 |
| Anti-BCMA CAR (21581 scFv) 2 × 10⁶ cells | 1.46E+06 ± 1.01E+05 |
| Anti-BCMA CAR (16747 scFv) 2 × 10⁶ cells | 1.32E+06 ± 5.86E+04 |
| | Radiance [p/s/cm2²/sr] 18 days post-implantation (mean ± SEM) |
| No tumor (background BLI) | 7.61E+05 ± 2.73E+04 |
| No CAR T (positive control) | 2.01E+07 ± 8.14E+05 |
| Control CAR T (Irrelevant scFv) 2 × 10⁶ cells | 2.11E+07 ± 3.02E+06 |
| Anti-BCMA CAR (21581 scFv) 2 × 10⁶ cells | 5.37E+06 ± 9.01E+05 |
| Anti-BCMA CAR (16747 scFv) 2 × 10⁶ cells | 6.98E+06 ± 9.57E+05 |
| | Radiance [p/s/cm2²/sr] 25 days post-implantation (mean ± SEM) |
| No tumor (background BLI) | 7.20E+05 ± 2.31E+04 |
| No CAR T (positive control) | 5.93E+07 ± 7.71E+06 |
| Control CAR T (Irrelevant scFv) 2 × 10⁶ cells | 6.40E+07 ± 1.71E+07 |
| Anti-BCMA CAR (21581 scFv) 2 × 10⁶ cells | 7.50E+05 ± 4.63E+04 |
| Anti-BCMA CAR (16747 scFv) 2 × 10⁶ cells | 6.77E+05 ± 7.41E+04 |
| | Radiance [p/s/cm2²/sr] 32 days post-implantation (mean ± SEM) |
| No tumor (background BLI) | 6.85E+05 ± 3.99E+04 |
| No CAR T (positive control) | Animals Euthanized |
| Control CAR T (Irrelevant scFv) 2 × 10⁶ cells | Animals Euthanized |
| Anti-BCMA CAR (21581 scFv) 2 × 10⁶ cells | 6.28E+05 ± 3.75E+04 |
| Anti-BCMA CAR (16747 scFv) 2 × 10⁶ cells | 6.82E+05 ± 2.35E+04 |

Example 6: BCMA-Specific CAR-T Cells Mediate Cytolysis of BCMA-Expressing Cells CD3+ T cells were isolated from human peripheral blood mononuclear cells (PBMCs), stimulated with CD3/CD28 microbeads plus 100 U/ml recombinant human IL-2, and transduced with the lentivirus at an MOI=5, as discussed above in Example 2. The transduced cells were expanded for 3 weeks with CD3/CD28 microbeads plus 100 U/ml recombinant human IL-2 before setting up a cytolytic assay.

To determine the cytolytic capacity of BCMA-targeted chimeric antigen receptor (CAR) T cells, a cytolytic assay was performed using expanded CAR-T cells and various tumor target cell lines that express variable levels of BCMA. On day 21 of expansion, the expanded CAR-T cells were co-cultured in triplicate at various ratios with calcein labeled BCMA+ target cell lines. Each target cell line was harvested and resupended at a density of 2×10⁶/mL before adding calcein-AM dye at a concentration of 8 uM for 35 minutes at 37° C. After calcein labeling, target cells were washed twice to remove extra calcein. Subsequently, T cells and target cells were co-cultured on a 96 well round bottom plate at various ratios and cultured at 37° C. for 2.5 hours when culture supernatant was harvested. For a negative control, target cells were co-cultured with T cells generated using a similar CAR designed to contain an irrelevant scFv that does not recognize BCMA. As an additional CAR negative control, untransduced and expanded T cells from the same normal healthy donor was used. As a control for antigen specific CAR-T cell mediated killing, the Chronic Myelogenous Leukemia K562 target cell line was used as this cell line is negative for BCMA expression. To determine if calcein is spontaneously released from the H-929 and MOLP-8 target cell lines, each cell line was cultured in the absence of CAR-T cells. To determine the maximum possible release of calcein, target cell lines were cultured and lysed using Optmizer media that was supplemented to contain 1% Triton™ X-114 detergent. Within the supernatant, the relative calcein levels were measured using a Viktor X4 plate reader and percent cytotoxicity was calculated as ((Calcein signal−Spontaneous Calcein Release)/(Calcein Maximum Release−Spontaneous Calcein Release))*100.

As shown in Tables 7A-7C, below, cultures consisting of BCMA-targeted CAR+ T cells generated using the 21581 and 16747 scFv induced robust cytolysis of H-929 target cells and MOLP-8 target cells. Relative to H-929 cells, a lower level of cytotoxicity was observed against MOLP8 cells. This result is explained by H-929 expressing higher levels of BCMA antigen than MOLP-8 cells. For each BCMA-targeted CAR-T cell culture, the greatest degree of cytotoxicity was observed against H-929 cells, and the BCMA-targeted CAR-T cells engineered with the 16747 scFv yielded the greatest magnitude of cytotoxicity against both target cell lines. Both the untransduced and expanded (MOI 0) T cells, and irrelevant CAR-T cells (17363), when co-cultured with target cells at the maximum ratio of 50 T cells to one target cell, failed to elicit any cytolysis of the MOLP-8 and H-929 target cells. This result illustrates that cytolysis is only observed when the CAR structure contains the scFv recognizing BCMA (e.g., from mAb21581 and mAb16747). In addition, the BCMA-targeted CAR-T cells demonstrated negligible cytotoxicity against K562 cells that lack BCMA expression indicating that BCMA expression is required for cytolysis to be observed.

TABLE 7A

| BCMA-Directed CAR-T Cell Cytolysis | | | | | | | | |
|---|---|---|---|---|---|---|---|---|
| T effector: | CAR-T cell/Target cell | | | | | | | |
| Target cell ratio | 21581/MOLP8 | | 21581/H929 | | 16747/MOLP8 | | 16747/H929 | |
| | mean | SD | mean | SD | mean | SD | mean | SD |
| 50 | 9.1 | 2.0 | 22.3 | 0.7 | 14.0 | 1.5 | 29.3 | 1.8 |
| 25 | 3.7 | 0.8 | 10.0 | 0.9 | 10.9 | 2.0 | 19.4 | 3.4 |
| 12.5 | 1.6 | 0.6 | 3.9 | 1.4 | 8.2 | 0.9 | 9.3 | 3.2 |
| 6.25 | 0.6 | 0.5 | 1.7 | 0.7 | 5.8 | 1.3 | 4.2 | 2.6 |
| 3.13 | −1.5 | 0.3 | 0.0 | 1.1 | 2.2 | 0.9 | 2.9 | 2.4 |
| 1.56 | 0.3 | 0.5 | −0.9 | 2.4 | 0.2 | 0.7 | 1.8 | 2.3 |
| 0.78 | −1.3 | 2.2 | −0.7 | 0.5 | −2.9 | 0.5 | 0.9 | 1.7 |

SD: standard deviation

TABLE 7B

| BCMA-Directed CAR-T Cell Cytolysis | | | | | | | | |
|---|---|---|---|---|---|---|---|---|
| T effector: Target cell | CAR-T cell/Target cell | | | | | | | |
| | 17363 HPV16/ MOLP8 | | 17363 HPV16/ H929 | | 21581/ K562 | | 16747/ K562 | |
| ratio | mean | SD | mean | SD | mean | SD | mean | SD |
| 50 | −3.1 | 1.7 | −0.8 | 1.2 | 2.0 | 1.1 | 3.5 | 1.4 |

SD: standard deviation

TABLE 7C

| BCMA-Directed CAR-T Cell Cytolysis | | | | |
|---|---|---|---|---|
| | CAR-T cell/Target cell | | | |
| T effector:Target | CAR Neg T cells/MOLP8 | | CAR Neg T cells/H929 | |
| cell ratio | mean | SD | mean | SD |
| 50 | −1.4 | 2.0 | −0.5 | 1.5 |

SD: standard deviation

Example 7: Ex Vivo Cytotoxicity of BCMA-Targeted CAR-T Cells in Multiple Myeloma Patient-Derived Bone Marrow CD3+ T cells were isolated from human peripheral blood mononuclear cells (PBMCs), stimulated with CD3/CD28 microbeads plus 100 U/ml recombinant human IL-2, and transduced with the lentivirus at an MOI=5, as discussed above in Example 2. The transduced cells were expanded for 3 weeks with CD3/CD28 microbeads plus 100 U/ml recombinant human IL-2 before setting up a cytotoxicity assay.

At harvest, expanding CAR-T cells were washed and resuspended in complete media (RPMI supplemented with 10% FBS, 100 U/mL penicillin, 100 μg/mL streptomycin, and 292 μg/mL L-glutamine). Bone marrow from multiple myeloma patients were thawed and resuspended in complete media. HS-5 stromal cells were plated into 96 well flat bottom plates at 10000 cells per well and incubated overnight. T cells and patient derived bone marrow were added to stromal containing wells at various E:T ratios (2 fold titrations starting at E:T=10:1) and cultured at 37° C. for 12 hours. As a CAR negative control, untransduced and expanded T cells from the same normal healthy donor was used.

After 12 hours, the multiple myeloma blasts survival was determined using flow cytometry. Cells were stained a cocktail of fluorophore-conjugated antibodies (anti-CD4, anti-CD8, anti-CD16, anti-CD45, anti-CD90, anti-CD138, and anti-SlamF7) in BD Horizon Brilliant Stain Buffer for 30 minutes at 4° C. Cells were washed once in PBS and stained with LIVE/DEAD Fixable Dead Cell Stain for 20-30 minutes at 4° C. followed by two washes in PBS and resuspended in cold Miltenyi AutoMacs Buffer. CountBright beads were added to the samples to quantify absolute cell counts per well. Samples were analyzed on a BD FortessaX20 flow cytometer. Surviving multiple myeloma blasts were gated as live single CD4−/CD8−/SlamF7+/CD138+. Percent survival was calculated as absolute count of live multiple myeloma blasts in the treated sample normalized to live multiple myeloma cells in untreated control.

Cultures consisting of BCMA-targeted CAR+ T cells generated using the mAb21581 VHNL induced robust target specific cytolysis of multiple myeloma blasts from 2 newly-diagnosed and 1 relapsed patient. At the E:T ratio 10:1 87-94% of multiple myeloma blasts were lysed. The untransduced and expanded (MOI 0) T cells lysed 34-0% of multiple myeloma blasts. This result demonstrates the ability of BCMA-targeted CAR+ T cells to potently lyse patient derived multiple myeloma blasts in a target specific manner. Results are shown in Table 8, below.

TABLE 8

% multiple myeloma blasts survival in BCMA-directed CAR-T cell cytolysis

| Sample ID | | | | | |
|---|---|---|---|---|---|
| MM453 | | MM511 | | MM455 | |
| Disease status | | | | | |
| newly diagnosed | | newly diagnosed | | relapsed | |
| % MM blasts | | | | | |
| 25% | | 38% | | 90% | |
| BCMA ABC on MM | | | | | |
| 12302 | | 2631 | | 46925 | |
| T cell:Target cell ratio | | | | | |
| BCMA CAR-T | control T | BCMA CAR-T | control T | BCMA CAR-T | control T |
| 10 | 7 | 66 | 11 | 85 | 13 | 156 |
| 5 | 15 | 66 | 19 | 91 | 32 | 155 |
| 2.5 | 23 | 90 | 28 | 82 | 81 | 148 |
| 1.25 | 49 | 77 | 37 | 92 | 81 | 104 |
| 0.625 | 82 | 92 | 56 | 92 | 98 | 112 |
| 0.312 | 108 | 92 | 100 | 100 | 98 | 102 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A B-cell maturation antigen (BCMA)-specific chimeric antigen receptor comprising, from N-terminus to C-terminus: (a) an extracellular ligand-binding domain comprising an anti-BCMA antigen-binding domain; (b) a hinge; (c) a transmembrane domain; and (d) a cytoplasmic domain comprising a costimulatory domain and a signaling domain, wherein the extracellular ligand-binding domain comprises an anti-BCMA single chain variable fragment (scFv) domain comprising a light chain variable region (LCVR) comprising complementarity determining regions LCDR1, LCDR2, and LCDR3 comprising the amino acid sequences, respectively, of SEQ ID NOs: 60, 62, and 64, and a heavy chain variable region (HCVR) comprising complementarity determining regions HCDR1, HCDR2, and HCDR3 comprising the amino acid sequences, respectively, of SEQ ID NOs: 52, 54, and 56.

2. The chimeric antigen receptor of claim 1, wherein the anti-BCMA scFv domain comprises a linker between the LCVR and the HCVR.

3. The chimeric antigen receptor of claim 1, further comprising a linker between the extracellular ligand-binding domain and the hinge.

4. The chimeric antigen receptor of claim 1, wherein the LCVR comprises the amino acid sequence of SEQ ID NO: 58, and the HCVR comprises the amino acid sequence of SEQ ID NO: 50.

5. The chimeric antigen receptor of claim 1, comprising the amino acid sequence of SEQ ID NO: 88.

6. An isolated nucleic acid molecule encoding the chimeric antigen receptor of claim 1.

7. A vector comprising the nucleic acid molecule of claim 6.

8. A cell comprising the isolated nucleic acid molecule of claim 6.

9. An engineered cell comprising a chimeric antigen receptor of claim 1.

10. The engineered cell of claim 9 that is an immune cell.

11. An engineered human T cell comprising a chimeric antigen receptor comprising, from N-terminus to C-terminus: (a) an extracellular ligand-binding domain comprising an anti-BCMA single chain variable fragment (scFv) domain comprising a light chain variable region (LCVR) and a heavy chain variable region (HCVR); (b) a hinge; (c) a transmembrane domain; and (d) a cytoplasmic domain comprising a 4-1BB costimulatory domain and a CD3zeta signaling domain, wherein the LCVR of the anti-BCMA scFv domain comprises complementarity determining regions LCDR1, LCDR2, and LCDR3 comprising the amino acid sequences, respectively, of SEQ ID NOs: 60, 62, and 64, and the HCVR of the anti-BCMA scFv domain comprises complementarity determining regions HCDR1, HCDR2, and HCDR3 comprising the amino acid sequences, respectively, of SEQ ID NOs: 52, 54, and 56.

12. The engineered human T cell of claim 11, wherein the scFv domain comprises a LCVR/HCVR amino acid sequence pair comprising the amino acid sequences of SEQ ID NOs: 58/50.

13. The engineered human T cell of claim 11:
(a) wherein the hinge comprises the amino acid sequence of SEQ ID NO: 97;
(b) wherein the transmembrane domain comprises the amino acid sequence of SEQ ID NO: 98;
(c) wherein the 4-1BB costimulatory domain comprises the amino acid sequence of SEQ ID NO: 99; or
(d) wherein the CD3zeta signaling domain comprises the amino acid sequence of SEQ ID NO: 100.

14. The engineered human T cell of claim 11, comprising a chimeric antigen receptor comprising the amino acid sequence of SEQ ID NO: 88.

15. A pharmaceutical composition comprising a genetically-modified human T cell and a pharmaceutically acceptable carrier, wherein the genetically-modified human T cell comprises a chimeric antigen receptor according to claim 1.

16. A method of engineering a population of cells to express a chimeric antigen receptor, comprising:
(a) providing a population of immune cells;
(b) introducing into the immune cells a nucleic acid molecule encoding a chimeric antigen receptor of claim 1;
(c) culturing the immune cells under conditions to express the nucleic acid molecules; and
(d) isolating the immune cells expressing the chimeric antigen receptor at the cells' surface.

17. The method of claim 16, further comprising obtaining the population of immune cells from a subject prior to introducing the nucleic acid molecule.

18. The isolated nucleic acid molecule of claim 6, comprising the nucleotide sequence of SEQ ID NO: 87.

19. The vector of claim 7, wherein the vector is a DNA vector, an RNA vector, a plasmid, a lentivirus vector, an adenovirus vector, or a retroviral vector.

20. The cell of claim 8, wherein the cell is a human T cell.

21. The engineered cell of claim 9, wherein the immune cell is an immune effector cell, a T lymphocyte, an inflammatory T lymphocyte, a cytotoxic T lymphocyte, a regulatory T lymphocyte, a helper T lymphocyte, or a CD8+ cytotoxic T lymphocyte.

22. The chimeric antigen receptor of claim 2, wherein the linker comprises an amino acid sequence selected from the group consisting of SEQ ID NOs: 93-96.

23. The chimeric antigen receptor of claim 22, wherein the linker comprises the amino acid sequence of SEQ ID NO: 95.

24. The chimeric antigen receptor of claim 1:
(a) wherein the hinge, the transmembrane domain, or both, are from a CD8a polypeptide;
(b) wherein the costimulatory domain comprises a 4-1BB costimulatory domain;
or
(c) wherein the signaling domain comprises a CD3zeta signaling domain.

25. The chimeric antigen receptor of claim 24:
(a) wherein the hinge comprises the amino acid sequence of SEQ ID NO: 97;
(b) wherein the transmembrane domain comprises the amino acid sequence of SEQ ID NO: 98;
(c) wherein the 4-1BB costimulatory domain comprises the amino acid sequence of SEQ ID NO: 99; or
(d) wherein the CD3zeta signaling domain comprises the amino acid sequence of SEQ ID NO: 100.

* * * * *

UNITED STATES PATENT AND TRADEMARK OFFICE
CERTIFICATE OF CORRECTION

PATENT NO. : 12,150,959 B2
APPLICATION NO. : 16/516060
DATED : November 26, 2024
INVENTOR(S) : David DiLillo et al.

It is certified that error appears in the above-identified patent and that said Letters Patent is hereby corrected as shown below:

In the Claims

Claim 24
Column 112, Line 34:
"CD8a"
Should read:
--CD8α--

Signed and Sealed this
Thirty-first Day of December, 2024

Derrick Brent
*Acting Director of the United States Patent and Trademark Office*

SEQUENCE LISTING

<160> NUMBER OF SEQ ID NOS: 101

<210> SEQ ID NO 1
<211> LENGTH: 366
<212> TYPE: DNA
<213> ORGANISM: Artificial Sequence
<220> FEATURE:
<223> OTHER INFORMATION: synthetic

<400> SEQUENCE: 1

```
caggtgcagc tggtggagtc gggggaggc gtggtccagc ctgggaggtc cctgagactc        60
tcctgtgcag cctctggatt caccttcagt acctatggca ttcactgggt ccgccaggct       120
ccaggcaagg ggctggagtg gtggcagtt atattacatg atggaagtag taactactat       180
gcagagtccg tgaagggccg attcatcatc tccagagaca attccaagaa cacactgtat       240
ctgcaaatga acagcctgag agctgaggac acggctctat attactgtac gaaaaggtat       300
tcagaagcag ctggcccaaa ttggttcgac ccctggggcc agggaaccct ggtcaccgtc       360
tcctca                                                                  366
```

<210> SEQ ID NO 2
<211> LENGTH: 122
<212> TYPE: PRT

```
<213> ORGANISM: Artificial Sequence
<220> FEATURE:
<223> OTHER INFORMATION: synthetic

<400> SEQUENCE: 2

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Ile His Trp Val Arg Gln Ala Pro Gly Lys Gly Leu Glu Trp Val
            35                  40                  45

Ala Val Ile Leu His Asp Gly Ser Ser Asn Tyr Tyr Ala Glu Ser Val
    50                  55                  60

Lys Gly Arg Phe Ile Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Thr Lys Arg Tyr Ser Glu Ala Ala Gly Pro Asn Trp Phe Asp Pro Trp
            100                 105                 110

Gly Gln Gly Thr Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct tcagtaccta tggc                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Thr Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atattacatg atggaagtag taac                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Leu His Asp Gly Ser Ser Asn
1               5
```

<210> SEQ ID NO 7
<211> LENGTH: 45
<212> TYPE: DNA
<213> ORGANISM: Artificial Sequence
<220> FEATURE:
<223> OTHER INFORMATION: synthetic

<400> SEQUENCE: 7
acgaaaaggt attcagaagc agctggccca aattggttcg acccc                45

<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

Thr Lys Arg Tyr Ser Glu Ala Ala Gly Pro Asn Trp Phe Asp Pro
1               5                   10                  15

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc gtgtctgcat ctgtaggaga cagagtcacc    60
atcacttgtc gggcgagtcg ggaattagc agctggttag cctggtatca gcagaagcca   120
gggaaagccc ctaagctcct gatccatgct gcatccagtt tgcaaagtgg ggtcccatca   180
aggttcagcg gcagtggatc tgggacagat ttcactctca ccatcagcag cctgcagcct   240
gaagattttg ctacttacta ttgtcaacag gctatcagtt tcccattcac tttcggccct   300
gggaccaaag tggatatcaa a                                             321

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Arg Gly Ile Ser Ser Trp
            20                  25                  30

Leu Ala Trp Tyr Gln Gln Lys Pro Gly Lys Ala Pro Lys Leu Leu Ile
        35                  40                  45

His Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Ser Phe Pro Phe
                85                  90                  95

Thr Phe Gly Pro Gly Thr Lys Val Asp Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cggggaatta gcagctgg                                                   18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Arg Gly Ile Ser Ser Trp
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                              9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacaggcta tcagtttccc attcact                                         27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Ala Ile Ser Phe Pro Phe Thr
1               5

<210> SEQ ID NO 17
<211> LENGTH: 360
<212> TYPE: DNA

```
<213> ORGANISM: Artificial Sequence
<220> FEATURE:
<223> OTHER INFORMATION: synthetic

<400> SEQUENCE: 17
gaggtgcagc tggtggagtc tgggggaggc ttggtacagc ctgggggtc cctgagactc      60 tcctgtgcag cctctggatt cacctttagc agctatgtca tgagttgggt ccgccaggct    120
ccagggaagg gactggagtg ggtctcagct attattggta gtggtggtag cacatattac    180
gcagactccg tgaagggccg gttcaccatc tccagagaca attccaagaa cacgctgtat    240
ctgcaaatga acagcctgag agccgaggac acggccgtat attactgtgc gaaaagagcc    300
ggggataact ggaactggtt cgacccctgg ggccaggaa  ccctggtcac cgtctcctca    360

<210> SEQ ID NO 18
<211> LENGTH: 120
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Ala Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ala Gly Asp Asn Trp Asn Trp Phe Asp Pro Trp Gly Gln
            100                 105                 110

Gly Thr Leu Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct ttagcagcta tgtc                                            24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Ser Tyr Val
1               5

<210> SEQ ID NO 21
```

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attattggta gtggtggtag caca                                            24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ile Gly Ser Gly Gly Ser Thr
1               5

<210> SEQ ID NO 23
<211> LENGTH: 39
<212> TYPE: DNA
<213> ORGANISM: Artificial Sequence
<220> FEATURE:
<223> OTHER INFORMATION: synthetic

<400> SEQUENCE: 23
gcgaaaagag ccggggataa ctggaactgg ttcgacccc                             39

<210> SEQ ID NO 24
<211> LENGTH: 13
<212> TYPE: PRT
<213> ORGANISM: Artificial Sequence
<220> FEATURE:
<223> OTHER INFORMATION: synthetic

<400> SEQUENCE: 24

Ala Lys Arg Ala Gly Asp Asn Trp Asn Trp Phe Asp Pro
1               5                   10

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcttcc gtgtctgcat ctttaggaga cagagtcacc     60
atcacttgtc gggcgagtca gggtattagc agctggttag cctggtatca gcggaaacca    120
gggaaagccc ctaagctcct gatctatgct gcatccagtt tgcaaagtgg ggtcccatca    180
aggttcagcg gcagtggatc tggggcggat tcactctca ccatcagcag cctgcagcct     240
gaagattttg caacttacta ttgtcaacag gctaaaagtg tcccattcac tttcggccct    300
gggaccaaag tggatatcaa a                                              321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

```
Asp Ile Gln Met Thr Gln Ser Pro Ser Ser Val Ser Ala Ser Leu Gly
1               5                   10                  15

Asp Arg Val Thr Ile Thr Cys Arg Ala Ser Gln Gly Ile Ser Ser Trp
            20                  25                  30

Leu Ala Trp Tyr Gln Arg Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Ala Lys Ser Val Pro Phe
                85                  90                  95

Thr Phe Gly Pro Gly Thr Lys Val Asp Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagggtatta gcagctgg                                                   18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

```
Gln Gly Ile Ser Ser Trp
1               5
```

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc                                                              9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

```
Ala Ala Ser
1
```

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
caacaggcta aaagtgtccc attcact                                      27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Ala Lys Ser Val Pro Phe Thr
1               5

<210> SEQ ID NO 33
<211> LENGTH: 351
<212> TYPE: DNA
<213> ORGANISM: Artificial Sequence
<220> FEATURE:
<223> OTHER INFORMATION: synthetic

<400> SEQUENCE: 33
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt atcagttgga atagtggtaa catgggatat   180
gcggactctg tgaagggccg attcaccatc tccagagaca acgccaagaa ctccctgttc   240
ctgcaaatgc acagtttgag agctgaggac acggcctttt attactgtgc aaaagtccgt   300
ctaactgcct ttgacttttg gggccaggga accctggtca ccgtctcctc a            351

<210> SEQ ID NO 34
<211> LENGTH: 117
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asn Met Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met His Ser Leu Arg Ala Glu Asp Thr Ala Phe Tyr Tyr Cys
                85                  90                  95

Ala Lys Val Arg Leu Thr Ala Phe Asp Phe Trp Gly Gln Gly Thr Leu
            100                 105                 110

Val Thr Val Ser Ser
        115

<210> SEQ ID NO 35
<211> LENGTH: 24
<212> TYPE: DNA
<213> ORGANISM: Artificial Sequence

```
<220> FEATURE:
<223> OTHER INFORMATION: synthetic

<400> SEQUENCE: 35
ggattcacct ttgatgatta tgcc                                          24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Asp Asp Tyr Ala
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
atcagttgga atagtggtaa catg                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Ser Trp Asn Ser Gly Asn Met
1               5

<210> SEQ ID NO 39
<211> LENGTH: 30
<212> TYPE: DNA
<213> ORGANISM: Artificial Sequence
<220> FEATURE:
<223> OTHER INFORMATION: synthetic

<400> SEQUENCE: 39
gcaaaagtcc gtctaactgc ctttgacttt                                    30

<210> SEQ ID NO 40
<211> LENGTH: 10
<212> TYPE: PRT
<213> ORGANISM: Artificial Sequence
<220> FEATURE:
<223> OTHER INFORMATION: synthetic

<400> SEQUENCE: 40

Ala Lys Val Arg Leu Thr Ala Phe Asp Phe
1               5                   10

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
```

```
gacatccaga tgacccagtc tccatcctcc ctgtctgcat ctgtaggaga cagagtcacc    60
atcacttgcc ggacaagtca gagcattggc aactatttaa attggtttca gcagaaacca   120
gggaaagccc ctaaactcct catctatact gcatccagtt tgcagaatgg agtcccatca   180
aggttcactg gcagtggatc tgggacagat ttcactctca ccatcagcag tctgcaacct   240
gaggattttg taatttacta ctgtcaacag agtttcagta ccccgtatac ttttggccag   300
gggaccaagc tggagatcaa a                                             321
```

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Gly Asn Tyr
            20                  25                  30

Leu Asn Trp Phe Gln Gln Lys Pro Gly Lys Ala Pro Lys Leu Leu Ile
        35                  40                  45

Tyr Thr Ala Ser Ser Leu Gln Asn Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Val Ile Tyr Tyr Cys Gln Gln Ser Phe Ser Thr Pro Tyr
                85                  90                  95

Thr Phe Gly Gln Gly Thr Lys Leu Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagagcattg gcaactat                                                  18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Gln Ser Ile Gly Asn Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 actgcatcc                                                                9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Thr Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
caacagagtt tcagtacccc gtatact                                           27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Ser Phe Ser Thr Pro Tyr Thr
1               5

<210> SEQ ID NO 49
<211> LENGTH: 354
<212> TYPE: DNA
<213> ORGANISM: Artificial Sequence
<220> FEATURE:
<223> OTHER INFORMATION: synthetic

<400> SEQUENCE: 49
caggtgcagc tggtggagtc tgggggaggc ttggtcaagc ctggagggtc cctgagactc        60
tcctgtgcag cctctggatt caccttcagt gactactaca tcagctggat ccgccaggct       120 ccagggaagg␣ggctggagtg␣ggtttcatac␣attagttcta␣gtggtagttc␣cataaagtac       180 gcagactctg tgaagggccg attcaccatc tccagggaca cgccaagaa ctcactgtat        240 ctgcaaatga acagcctgag agccgaggac acggccgtat attactgtgc gagagaggga       300 gggaactacg␣gtatggacgt␣ctggggccaa␣gggaccacgg␣tcaccgtctc␣ctca            354

<210> SEQ ID NO 50
<211> LENGTH: 118
<212> TYPE: PRT
<213> ORGANISM: Artificial Sequence
<220> FEATURE:
<223> OTHER INFORMATION: synthetic

<400> SEQUENCE: 50

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Ile Ser Trp Ile Arg Gln Ala Pro Gly Lys Gly Leu Glu Trp Val

```
                    35                  40                  45
Ser Tyr Ile Ser Ser Gly Ser Ser Ile Lys Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Gly Asn Tyr Gly Met Asp Val Trp Gly Gln Gly Thr
                100                 105                 110

Thr Val Thr Val Ser Ser
        115
```

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcacct tcagtgacta ctac                                        24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Ser Asp Tyr Tyr
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
attagttcta gtggtagttc cata                                        24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Ser Ser Gly Ser Ser Ile
1               5

<210> SEQ ID NO 55
<211> LENGTH: 33
<212> TYPE: DNA
<213> ORGANISM: Artificial Sequence
<220> FEATURE:
<223> OTHER INFORMATION: synthetic

<400> SEQUENCE: 55
gcgagagagg gagggaacta cggtatggac gtc                              33

<210> SEQ ID NO 56
<211> LENGTH: 11
<212> TYPE: PRT
<213> ORGANISM: Artificial Sequence
<220> FEATURE:
<223> OTHER INFORMATION: synthetic

<400> SEQUENCE: 56

Ala Arg Glu Gly Gly Asn Tyr Gly Met Asp Val
1               5                   10

<210> SEQ ID NO 57
<211> LENGTH: 321
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcttcc gtgtctgcat ctgtaggaga cagagtcacc      60
atcacttgtc gggcgagtca gggtattaac aactggttag tctggtatca gcagaaacca     120
gggaaagccc ctaagctcct gatctatgct gcaaccagct tgcaaagtgg ggtcccatca     180
aggttcagcg gcagtgggtc tgggacagat ttcactctca ccatcagcag cctgcagcct     240
gaagattttg caacttacta ttgtcaacag gctaacagtt tccctcccac ttttggccag     300
gggaccaagc tggagatcaa a                                               321

<210> SEQ ID NO 58
<211> LENGTH: 107
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Asn Trp
            20                  25                  30

Leu Val Trp Tyr Gln Gln Lys Pro Gly Lys Ala Pro Lys Leu Leu Ile
        35                  40                  45

Tyr Ala Ala Thr Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagggtatta acaactgg                                                    18

```
<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Gly Ile Asn Asn Trp
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcaacc                                                                9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Thr
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
caacaggcta acagtttccc tcccact                                           27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Ala Asn Ser Phe Pro Pro Thr
1               5

<210> SEQ ID NO 65
<211> LENGTH: 375
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttggtccagc ctggggggtc cctgagactc       60
tcctgtgcag cctctggatt cacctttagt aacttttgga tgacctgggt ccgccaggct      120
ccagggaagg ggctggagtg ggtggccaac atgaaccaag atggaagtga aaatactat       180 gtggactctg tgaagggccg attcaccatc tccagagaca cgccaagag ctcactgtat       240
```

```
ctgcaaatga acagcctgag agccgaggac acggctgtgt attactgtgc gagagatcgg      300
gaatattgta ttagtaccag ctgctatgat gactttgact actggggcca gggaaccctg      360
gtcaccgtct cctca                                                        375
```

```
<210> SEQ ID NO 66
<211> LENGTH: 125
<212> TYPE: PRT
<213> ORGANISM: Artificial Sequence
<220> FEATURE:
<223> OTHER INFORMATION: synthetic

<400> SEQUENCE: 66
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Trp Met Thr Trp Val Arg Gln Ala Pro Gly Lys Gly Leu Glu Trp Val
        35                  40                  45

Ala Asn Met Asn Gln Asp Gly Ser Glu Lys Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Glu Tyr Cys Ile Ser Thr Ser Cys Tyr Asp Asp Phe
            100                 105                 110

Asp Tyr Trp Gly Gln Gly Thr Leu Val Thr Val Ser Ser
        115                 120                 125

```
<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct ttagtaactt ttgg                                              24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68
```

Gly Phe Thr Phe Ser Asn Phe Trp
1               5

```
<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
atgaaccaag atggaagtga gaaa                                              24
```

```
<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Met Asn Gln Asp Gly Ser Glu Lys
1               5

<210> SEQ ID NO 71
<211> LENGTH: 54
<212> TYPE: DNA
<213> ORGANISM: Artificial Sequence
<220> FEATURE:
<223> OTHER INFORMATION: synthetic

<400> SEQUENCE: 71
gcgagagatc gggaatattg tattagtacc agctgctatg atgactttga ctac        54

<210> SEQ ID NO 72
<211> LENGTH: 18
<212> TYPE: PRT
<213> ORGANISM: Artificial Sequence
<220> FEATURE:
<223> OTHER INFORMATION: synthetic

<400> SEQUENCE: 72

Ala Arg Asp Arg Glu Tyr Cys Ile Ser Thr Ser Cys Tyr Asp Asp Phe
1               5                   10                  15

Asp Tyr

<210> SEQ ID NO 73
<211> LENGTH: 324
<212> TYPE: DNA
<213> ORGANISM: Artificial Sequence
<220> FEATURE:
<223> OTHER INFORMATION: synthetic

<400> SEQUENCE: 73
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcatagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 74
<211> LENGTH: 108
<212> TYPE: PRT
<213> ORGANISM: Artificial Sequence
<220> FEATURE:
<223> OTHER INFORMATION: synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

Tyr Ala Ala Ser Ser Leu His Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
                100                 105

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75
cagagcatta gcagctat                                           18

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Ser Ile Ser Ser Tyr
 1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctgcatcc                                                      9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Ala Ser
 1

<210> SEQ ID NO 79
<211> LENGTH: 30
<212> TYPE: DNA
<213> ORGANISM: Artificial Sequence
<220> FEATURE:
<223> OTHER INFORMATION: synthetic

<400> SEQUENCE: 79
caacagagtt acagtacccc tccgatcacc                              30

<210> SEQ ID NO 80
<211> LENGTH: 10
<212> TYPE: PRT

<210> SEQ ID NO 81
<211> LENGTH: 1404
<212> TYPE: DNA
<213> ORGANISM: Artificial Sequence
<220> FEATURE:
<223> OTHER INFORMATION: synthetic

<400> SEQUENCE: 80

Gln Gln Ser Tyr Ser Thr Pro Pro Ile Thr
1               5                   10

<210> SEQ ID NO 81
<211> LENGTH: 1404
<212> TYPE: DNA
<213> ORGANISM: Artificial Sequence
<220> FEATURE:
<223> OTHER INFORMATION: BCMA 16711 (VL-VH) ScFv CAR-T
    (16711_VK_v2(human).(G4S)3 Linker.16711 VH.hCD8a
    hinge/TM.hCD137 (4-1BB).hCD3 zeta)

<400> SEQUENCE: 81

```
gacatccaga tgacccagtc tccatcctcc gtgtctgcat ctgtaggaga cagagtcacc    60
atcacttgtc gggcgagtcg gggaattagc agctggttag cctggtatca gcagaagcca   120
gggaaagccc ctaagctcct gatccatgct gcatccagtt tgcaaagtgg ggtcccatca   180
aggttcagcg gcagtggatc tgggacagat ttcactctca ccatcagcag cctgcagcct   240
gaagattttg ctacttacta ttgtcaacag gctatcagtt tcccattcac tttcggccct   300
gggaccaaag tggatatcaa aggcggcggt ggatctggag gcggtggaag cggtggcggg   360
ggaagtcagg tgcagctggt ggagtcgggg ggaggcgtgg tccagcctgg aggtccctg    420
agactctcct gtgcagcctc tggattcacc ttcagtacct atggcattca ctgggtccgc   480
caggctccag gcaaggggct ggagtgggtg gcagttatat acatgatgg aagtagtaac   540
tactatgcag agtccgtgaa gggccgattc atcatctcca gagacaattc caagaacaca   600
ctgtatctgc aaatgaacag cctgagagct gaggacacgg ctctatatta ctgtacgaaa   660
aggtattcag aagcagctgg cccaaaattgg ttcgacccct ggggccaggg aaccctggtc   720
accgtctcct caactaccac tcctgctccc cgccccccaa cacctgctcc aactattgca   780
tcccaaccac tctccctcag acccgaagct tgtcgcccc cgccggagg tgctgttcac    840
actagaggac tcgattttgc ttgcgacatt tatatctggg ccccacttgc aggtacttgc   900
ggagtattgc tgctctcact tgttattact ctttattgca acggggcag aaagaaactc   960
ctgtatatat tcaaacaacc atttatgaga ccagtacaaa ctactcaaga ggaagatggc  1020
tgtagctgcc gatttccaga agaagaagaa ggaggatgtg aactgagagt gaagttcagc  1080
aggagcgcag acgccccccgc gtacaagcag ggccagaacc agctctataa cgagctcaat  1140
ctaggacgaa gagaggagta cgatgttttg gacaagagac gtggccggga ccctgagatg  1200
gggggaaagc cgagaaggaa gaaccctcag gaaggcctgt acaatgaact gcagaaagat  1260
aagatggcgg aggcctacag tgagattggg atgaaaggcg agcgccggag gggcaagggg  1320
cacgatggcc tttaccaggg tctcagtaca gccaccaagg acacctacga cgcccttcac  1380
atgcaggccc tgccccctcg ctaa                                         1404
```

<210> SEQ ID NO 82
<211> LENGTH: 467
<212> TYPE: PRT
<213> ORGANISM: Artificial Sequence
<220> FEATURE:
<223> OTHER INFORMATION: BCMA 16711 (VL-VH) ScFv CAR-T
    (16711_VK_v2(human).(G4S)3 Linker.16711 VH.hCD8a
    hinge/TM.hCD137 (4-1BB).hCD3 zeta)

```
<400> SEQUENCE: 82

Asp Ile Gln Met Thr Gln Ser Pro Ser Val Ser Ala Ser Val Gly
1               5                   10                  15

Asp Arg Val Thr Ile Thr Cys Arg Ala Ser Arg Gly Ile Ser Ser Trp
            20                  25                  30

Leu Ala Trp Tyr Gln Gln Lys Pro Gly Lys Ala Pro Lys Leu Leu Ile
        35                  40                  45

His Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Ser Phe Pro Phe
                85                  90                  95

Thr Phe Gly Pro Gly Thr Lys Val Asp Ile Lys Gly Gly Gly Gly Ser
            100                 105                 110

Gly Gly Gly Gly Ser Gly Gly Gly Ser Gln Val Gln Leu Val Glu
            115                 120                 125

Ser Gly Gly Val Val Gln Pro Gly Arg Ser Leu Arg Leu Ser Cys
130                 135                 140

Ala Ala Ser Gly Phe Thr Phe Ser Thr Tyr Gly Ile His Trp Val Arg
145                 150                 155                 160

Gln Ala Pro Gly Lys Gly Leu Glu Trp Val Ala Val Ile Leu His Asp
            165                 170                 175

Gly Ser Ser Asn Tyr Tyr Ala Glu Ser Val Lys Gly Arg Phe Ile Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Leu Tyr Tyr Cys Thr Lys Arg Tyr Ser Glu
    210                 215                 220

Ala Ala Gly Pro Asn Trp Phe Asp Pro Trp Gly Gln Gly Thr Leu Val
225                 230                 235                 240

Thr Val Ser Ser Thr Thr Thr Pro Ala Pro Arg Pro Pro Thr Pro Ala
            245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
            275                 280                 285

Asp Ile Tyr Ile Trp Ala Pro Leu Ala Gly Thr Cys Gly Val Leu Leu
            290                 295                 300

Leu Ser Leu Val Ile Thr Leu Tyr Cys Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Arg Val Lys Phe Ser Arg Ser Ala Asp Ala Pro Ala Tyr
            355                 360                 365

Lys Gln Gly Gln Asn Gln Leu Tyr Asn Glu Leu Asn Leu Gly Arg Arg
            370                 375                 380

Glu Glu Tyr Asp Val Leu Asp Lys Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415
```

Leu Gln Lys Asp Lys Met Ala Glu Ala Tyr Ser Glu Ile Gly Met Lys
              420                 425                 430

Gly Glu Arg Arg Arg Gly Lys Gly His Asp Gly Leu Tyr Gln Gly Leu
              435                 440                 445

Ser Thr Ala Thr Lys Asp Thr Tyr Asp Ala Leu His Met Gln Ala Leu
              450                 455                 460

Pro Pro Arg
465

<210> SEQ ID NO 83
<211> LENGTH: 1398
<212> TYPE: DNA
<213> ORGANISM: Artificial Sequence
<220> FEATURE:
<223> OTHER INFORMATION: BCMA 16716 (VL-VH) ScFv CAR-T
      (16716_VK(human).(G4S)3
      Linker.16716_VH(human).hCD8a hinge/TM.hCD137
      (4-1BB).hCD3 zeta)

<400> SEQUENCE: 83
gacatccaga tgacccagtc tccatcttcc gtgtctgcat ctttaggaga cagagtcacc      60
atcacttgtc gggcgagtca gggtattagc agctggttag cctggtatca gcggaaacca     120
gggaaagccc ctaagctcct gatctatgct gcatccagtt tgcaaagtgg ggtcccatca     180
aggttcagcg gcagtggatc tggggcggat ttcactctca ccatcagcag cctgcagcct     240
gaagattttg caacttacta ttgtcaacag gctaaaagtg tcccattcac tttcggccct     300
gggaccaaag tggatatcaa aggcggcggt ggatctggag cggtggaag cggtggcggg      360
ggaagtgagg tgcagctggt ggagtctggg ggaggcttgg tacagcctgg ggggtccctg     420
agactctcct gtgcagcctc tggattcacc tttagcagct atgtcatgag ttgggtccgc     480
caggctccag ggaagggact ggagtgggtc tcagctatta ttggtagtgg tggtagcaca     540
tattacgcag actccgtgaa gggccggttc accatctcca gagacaattc caagaacacg     600
ctgtatctgc aaatgaacag cctgagagcc gaggacacgg ccgtatatta ctgtgcgaaa     660
agagccgggg ataactggaa ctggttcgac ccctggggcc agggaaccct ggtcaccgtc     720
tcctcaacta ccactcctgc tccccgcccc ccaacacctg ctccaactat gcatcccaa      780
ccactctccc tcagacccga gcttgtcgc ccgccgccg gaggtgctgt tcacactaga      840
ggactcgatt ttgcttgcga catttatatc tgggcccac ttgcaggtac ttgcggagta      900
ttgctgctct cacttgttat tactctttat gcaaacggg gcagaaagaa actcctgtat     960
atattcaaac aaccatttat gagaccagta caaactactc aagaggaaga tggctgtagc    1020
tgccgatttc cagaagaaga agaaggagga tgtgaactga gagtgaagtt cagcaggagc    1080
gcagacgccc ccgcgtacaa gcagggccag aaccagctct ataacgagct caatctagga    1140
cgaagagagg agtacgatgt tttggacaag acgtggcc gggaccctga tggggggga      1200
aagccgagaa ggaagaaccc tcaggaaggc ctgtacaatg aactgcagaa agataagatg    1260
gcggaggcct acagtgagat tgggatgaaa ggcgagcgcc ggaggggcaa ggggcacgat    1320
ggcctttacc agggtctcag tacagccacc aaggacacct cgacgccct tcacatgcag     1380
gccctgcccc ctcgctaa                                                  1398

<210> SEQ ID NO 84
<211> LENGTH: 465
<212> TYPE: PRT
<213> ORGANISM: Artificial Sequence
<220> FEATURE:
<223> OTHER INFORMATION: BCMA 16716 (VL-VH) ScFv CAR-T
(16716_VK(human).(G4S)3
Linker.16716_VH(human).hCD8a hinge/TM.hCD137
(4-1BB).hCD3 zeta)

<400> SEQUENCE: 84

```
Asp Ile Gln Met Thr Gln Ser Pro Ser Ser Val Ser Ala Ser Leu Gly
1               5                   10                  15

Asp Arg Val Thr Ile Thr Cys Arg Ala Ser Gln Gly Ile Ser Ser Trp
            20                  25                  30

Leu Ala Trp Tyr Gln Arg Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Ala Lys Ser Val Pro Phe
                85                  90                  95

Thr Phe Gly Pro Gly Thr Lys Val Asp Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Phe Thr Phe Ser Ser Tyr Val Met Ser Trp Val Arg
145                 150                 155                 160

Gln Ala Pro Gly Lys Gly Leu Glu Trp Val Ser Ala Ile Ile Gly Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Lys Arg Ala Gly Asp
    210                 215                 220

Asn Trp Asn Trp Phe Asp Pro Trp Gly Gln Gly Thr Leu Val Thr Val
225                 230                 235                 240

Ser Ser Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Lys Gln
        355                 360                 365

Gly Gln Asn Gln Leu Tyr Asn Glu Leu Asn Leu Gly Arg Arg Glu Glu
    370                 375                 380
```

```
Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
            405                 410                 415

Lys Asp Lys Met Ala Glu Ala Tyr Ser Glu Ile Gly Met Lys Gly Glu
        420                 425                 430

Arg Arg Arg Gly Lys Gly His Asp Gly Leu Tyr Gln Gly Leu Ser Thr
    435                 440                 445

Ala Thr Lys Asp Thr Tyr Asp Ala Leu His Met Gln Ala Leu Pro Pro
        450                 455                 460

Arg
465

<210> SEQ ID NO 85
<211> LENGTH: 1389
<212> TYPE: DNA
<213> ORGANISM: Artificial Sequence
<220> FEATURE:
<223> OTHER INFORMATION: BCMA 16732 (VL-VH) ScFv CAR-T
      (16732_VK_v2(human).(G4S)3
      Linker.16732_VH(human).hCD8a hinge/TM.hCD137
      (4-1BB).hCD3 zeta)

<400> SEQUENCE: 85
gacatccaga tgacccagtc tccatcctcc ctgtctgcat ctgtaggaga cagagtcacc      60
atcacttgcc ggacaagtca gagcattggc aactatttaa attggtttca gcagaaacca    120
gggaaagccc ctaaactcct catctatact gcatccagtt tgcagaatgg agtcccatca    180
aggttcactg gcagtggatc tgggacagat ttcactctca ccatcagcag tctgcaacct    240
gaggattttg taatttacta ctgtcaacag agtttcagta ccccgtatac ttttggccag    300
gggaccaagc tggagatcaa aggcggcggt ggatctggag gcggtggaag cggtggcggg    360
ggaagtgaag tgcagctggt ggagtctggg ggaggcttgg tacagcctgg caggtccctg    420
agactctcct gtgcagcctc tggattcacc tttgatgatt atgccatgca ctgggtccgg    480
caagctccag ggaagggcct ggagtgggtc tcaggtatca gttggaatag tggtaacatg    540
ggatatgcgg actctgtgaa gggccgattc accatctcca gagacaacgc caagaactcc    600
ctgttcctgc aaatgcacag tttgagagct gaggacacgg cctttttatta ctgtgcaaaa    660 gtccgtctaa ctgcctttga cttttgggc agggaaccc tggtcaccgt ctcctcaact    720
accactcctg ctccccgccc cccaacacct gctccaacta ttgcatccca accactctcc    780
ctcagacccg aagcttgtcg ccccgccgcc ggaggtgctg ttcacactag aggactcgat    840
tttgcttgcg acatttatat ctgggcccca cttgcaggta cttgcggagt attgctgctc    900
tcacttgtta ttactcttta ttgcaaacgg ggcagaaaga aactcctgta tatattcaaa    960
caaccattta tgagaccagt acaaactact caagaggaag atggctgtag ctgccgattt   1020
ccagaagaag aagaaggagg atgtgaactg agagtgaagt tcagcaggag cgcagacgcc   1080
cccgcgtaca gcagggcca gaaccagctc tataacgagc tcaatctagg acgaagagag   1140
gagtacgatg ttttggacaa gagacgtggc cgggaccctg agatgggggg aaagccgaga   1200
aggaagaacc ctcaggaagg cctgtacaat gaactgcaga agataagat ggcggaggcc   1260 tacagtgaga ttgggatgaa aggcgagcgc cggaggggca aggggcacga tggcctttac   1320
cagggtctca gtacagccac caaggacacc tacgacgccc ttcacatgca ggccctgccc   1380
cctcgctaa                                                           1389
```

<210> SEQ ID NO 86
<211> LENGTH: 462
<212> TYPE: PRT
<213> ORGANISM: Artificial Sequence
<220> FEATURE:
<223> OTHER INFORMATION: BCMA 16732 (VL-VH) ScFv CAR-T
(16732_VK_v2(human).(G4S)3
Linker.16732_VH(human).hCD8a hinge/TM.hCD137
(4-1BB).hCD3 zeta)

<400> SEQUENCE: 86

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Gly Asn Tyr
            20                  25                  30

Leu Asn Trp Phe Gln Gln Lys Pro Gly Lys Ala Pro Lys Leu Leu Ile
        35                  40                  45

Tyr Thr Ala Ser Ser Leu Gln Asn Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Val Ile Tyr Tyr Cys Gln Gln Ser Phe Ser Thr Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Arg Ser Leu Arg Leu Ser Cys
130                 135                 140

Ala Ala Ser Gly Phe Thr Phe Asp Asp Tyr Ala Met His Trp Val Arg
145                 150                 155                 160

Gln Ala Pro Gly Lys Gly Leu Glu Trp Val Ser Gly Ile Ser Trp Asn
                165                 170                 175

Ser Gly Asn Met Gly Tyr Ala Asp Ser Val Lys Gly Arg Phe Thr Ile
            180                 185                 190

Ser Arg Asp Asn Ala Lys Asn Ser Leu Phe Leu Gln Met His Ser Leu
        195                 200                 205

Arg Ala Glu Asp Thr Ala Phe Tyr Tyr Cys Ala Lys Val Arg Leu Thr
    210                 215                 220

Ala Phe Asp Phe Trp Gly Gln Gly Thr Leu Val Thr Val Ser Ser Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Ile Tyr Ile Trp
        275                 280                 285

Ala Pro Leu Ala Gly Thr Cys Gly Val Leu Leu Leu Ser Leu Val Ile
    290                 295                 300

Thr Leu Tyr Cys Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Glu Gly Gly Cys Glu Leu Arg Val
            340                 345                 350
```

```
Lys Phe Ser Arg Ser Ala Asp Ala Pro Ala Tyr Lys Gln Gly Gln Asn
            355                 360                 365

Gln Leu Tyr Asn Glu Leu Asn Leu Gly Arg Arg Glu Glu Tyr Asp Val
        370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 87
<211> LENGTH: 1392
<212> TYPE: DNA
<213> ORGANISM: Artificial Sequence
<220> FEATURE:
<223> OTHER INFORMATION: BCMA 16747 (VL-VH) ScFv CAR-T
      (16747_VK(human).(G4S)3
      Linker.16747_VH(human).hCD8a hinge/TM.hCD137
      (4-1BB).hCD3 zeta)

<400> SEQUENCE: 87
```

| | | | | | |
|---|---|---|---|---|---|
| gacatccaga | tgacccagtc | tccatcttcc | gtgtctgcat | ctgtaggaga | cagagtcacc | 60 |
| atcacttgtc | gggcgagtca | gggtattaac | aactggttag | tctggtatca | gcagaaacca | 120 |
| gggaaagccc | ctaagctcct | gatctatgct | gcaaccagct | tgcaaagtgg | ggtcccatca | 180 |
| aggttcagcg | gcagtgggtc | tgggacagat | ttcactctca | ccatcagcag | cctgcagcct | 240 |
| gaagattttg | caacttacta | ttgtcaacag | gctaacagtt | tccctcccac | ttttggccag | 300 |
| gggaccaagc | tggagatcaa | aggcggcggt | ggatctggag | gcggtggaag | cggtggcggg | 360 |
| ggaagtcagg | tgcagctggt | ggagtctggg | ggaggcttgg | tcaagcctgg | agggtccctg | 420 |
| agactctcct | gtgcagcctc | tggattcacc | ttcagtgact | actacatcag | ctggatccgc | 480 |
| caggctccag | ggaaggggct | ggagtgggtt | tcatacatta | gttctagtgg | tagttccata | 540 |
| aagtacgcag | actctgtgaa | gggccgattc | accatctcca | gggacaacgc | caagaactca | 600 |
| ctgtatctgc | aaatgaacag | cctgagagcc | gaggacacgg | ccgtatatta | ctgtgcgaga | 660 |
| gagggaggga | actacggtat | ggacgtctgg | ggccaaggga | ccacggtcac | cgtctcctca | 720 |
| actaccactc | ctgctccccg | ccccccaaca | cctgctccaa | ctattgcatc | caaccactc | 780 |
| tccctcagac | ccgaagcttg | tcgccccgcc | gccggaggtg | ctgttcacac | tagaggactc | 840 |
| gatttttgctt | gcgacattta | tatctgggcc | ccacttgcag | gtacttgcgg | agtattgctg | 900 |
| ctctcacttg | ttattactct | ttattgcaaa | cggggcagaa | agaaactcct | gtatatattc | 960 |
| aaacaaccat | ttatgagacc | agtacaaact | actcaagagg | aagatggctg | tagctgccga | 1020 |
| tttccagaag | aagaagaagg | aggatgtgaa | ctgagagtga | agttcagcag | gagcgcagac | 1080 |
| gcccccgcgt | acaagcaggg | ccagaaccag | ctctataacg | agctcaatct | aggacgaaga | 1140 |
| gaggagtacg | atgttttgga | caagagacgt | ggccgggacc | ctgagatggg | gggaaagccg | 1200 |
| agaaggaaga | accctcagga | aggcctgtac | aatgaactgc | agaaagataa | gatggcggag | 1260 |
| gcctacagtg | agattgggat | gaaaggcgag | cgccggaggg | gcaaggggca | cgatggcctt | 1320 |

```
taccagggtc tcagtacagc caccaaggac acctacgacg ccttcacat gcaggccctg   1380 ccccctcgct aa                                                       1392
```

<210> SEQ ID NO 88
<211> LENGTH: 463
<212> TYPE: PRT
<213> ORGANISM: Artificial Sequence
<220> FEATURE:
<223> OTHER INFORMATION: BCMA 16747 (VL-VH) ScFv CAR-T
      (16747_VK(human).(G4S)3
      Linker.16747_VH(human).hCD8a hinge/TM.hCD137
      (4-1BB).hCD3 zeta)

<400> SEQUENCE: 88

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Asn Trp
            20                  25                  30

Leu Val Trp Tyr Gln Gln Lys Pro Gly Lys Ala Pro Lys Leu Leu Ile
        35                  40                  45

Tyr Ala Ala Thr Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Val Glu
        115                 120                 125

Ser Gly Gly Gly Leu Val Lys Pro Gly Gly Ser Leu Arg Leu Ser Cys
130                 135                 140

Ala Ala Ser Gly Phe Thr Phe Ser Asp Tyr Tyr Ile Ser Trp Ile Arg
145                 150                 155                 160

Gln Ala Pro Gly Lys Gly Leu Glu Trp Val Ser Tyr Ile Ser Ser Ser
                165                 170                 175

Gly Ser Ser Ile Lys Tyr Ala Asp Ser Val Lys Gly Arg Phe Thr Ile
            180                 185                 190

Ser Arg Asp Asn Ala Lys Asn Ser Leu Tyr Leu Gln Met Asn Ser Leu
        195                 200                 205

Arg Ala Glu Asp Thr Ala Val Tyr Tyr Cys Ala Arg Glu Gly Gly Asn
210                 215                 220

Tyr Gly Met Asp Val Trp Gly Gln Gly Thr Thr Val Thr Val Ser Ser
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Tyr Ile
        275                 280                 285

Trp Ala Pro Leu Ala Gly Thr Cys Gly Val Leu Leu Leu Ser Leu Val
290                 295                 300

Ile Thr Leu Tyr Cys Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335
```

```
Cys Ser Cys Arg Phe Pro Glu Glu Glu Gly Gly Cys Glu Leu Arg
            340                 345                 350

Val Lys Phe Ser Arg Ser Ala Asp Ala Pro Ala Tyr Lys Gln Gly Gln
355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
                435                 440                 445

Lys Asp Thr Tyr Asp Ala Leu His Met Gln Ala Leu Pro Pro Arg
        450                 455                 460

<210> SEQ ID NO 89
<211> LENGTH: 1431
<212> TYPE: DNA
<213> ORGANISM: Artificial Sequence
<220> FEATURE:
<223> OTHER INFORMATION: BCMA 21581 (VL-VH) ScFv CAR-T
      (21581 VK(human).(G4S)3 Linker.21581
      VH(human).G4S Linker_v2.hCD8a hinge/TM.hCD137
      (4-1BB).hCD3 zeta)

<400> SEQUENCE: 89
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcatagtgg ggtcccatca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaaggcggc ggtggatctg gaggcggtgg aagcggtggc     360 ggggaagtg aggtgcagct ggtggagtct ggggggaggct tggtccagcc tggggggtcc     420
ctgagactct cctgtgcagc ctctggattc acctttagta actttggat gacctgggtc     480 cgccaggctc cagggaaggg gctggagtgg gtggccaaca tgaaccaaga tggaagtgag     540
aaatactatg tggactctgt gaagggccga ttcaccatct ccagagacaa cgccaagagc     600
tcactgtatc tgcaaatgaa cagcctgaga gccgaggaca cggctgtgta ttactgtgcg     660
agagatcggg aatattgtat tagtaccagc tgctatgatg actttgacta ctggggccag     720
ggaaccctgg tcaccgtctc ctcaggaggc ggaggcagca ctaccactcc tgctccccgc     780
cccccaacac ctgctccaac tattgcatcc aaccactct cctcagacc cgaagcttgt      840 cgccccgccg ccggaggtgc tgttcacact agaggactcg attttgcttg cgacatttat     900
atctgggccc cacttgcagg tacttgcgga gtattgctgc tctcacttgt tattactctt     960
tattgcaaac ggggcagaaa gaaactcctg tatatattca acaaccatt tatgagacca     1020 gtacaaacta ctcaagagga gatggctgt agctgccgat tccagaaga agaagaagga     1080 ggatgtgaac tgagagtgaa gttcagcagg agcgcagacg cccccgcgta caagcagggc     1140
cagaaccagc tctataacga gctcaatcta ggacgaagag aggagtacga tgttttggac     1200
aagagacgtg gccgggaccc tgagatgggg ggaaagccga aaggaagaa ccctcaggaa     1260
```

```
ggcctgtaca atgaactgca gaaagataag atggcggagg cctacagtga gattgggatg    1320
aaaggcgagc gccggagggg caagggcac gatggccttt accagggtct cagtacagcc    1380
accaaggaca cctacgacgc ccttcacatg caggccctgc cccctcgcta a             1431
```

<210> SEQ ID NO 90
<211> LENGTH: 476
<212> TYPE: PRT
<213> ORGANISM: Artificial Sequence
<220> FEATURE:
<223> OTHER INFORMATION: BCMA 21581 (VL-VH) ScFv CAR-T
      (21581 VK(human).(G4S)3 Linker.21581
      VH(human).G4S Linker_v2.hCD8a hinge/TM.hCD137
      (4-1BB).hCD3 zeta)

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Phe Ser Asn Phe Trp Met Thr Trp Val
145                 150                 155                 160

Arg Gln Ala Pro Gly Lys Gly Leu Glu Trp Val Ala Asn Met Asn Gln
                165                 170                 175

Asp Gly Ser Glu Lys Tyr Tyr Val Asp Ser Val Lys Gly Arg Phe Thr
            180                 185                 190

Ile Ser Arg Asp Asn Ala Lys Ser Ser Leu Tyr Leu Gln Met Asn Ser
        195                 200                 205

Leu Arg Ala Glu Asp Thr Ala Val Tyr Tyr Cys Ala Arg Asp Arg Glu
    210                 215                 220

Tyr Cys Ile Ser Thr Ser Cys Tyr Asp Asp Phe Asp Tyr Trp Gly Gln
225                 230                 235                 240

Gly Thr Leu Val Thr Val Ser Ser Gly Gly Gly Gly Ser Thr Thr Thr
                245                 250                 255

Pro Ala Pro Arg Pro Pro Thr Pro Ala Pro Thr Ile Ala Ser Gln Pro
            260                 265                 270

Leu Ser Leu Arg Pro Glu Ala Cys Arg Pro Ala Ala Gly Gly Ala Val
        275                 280                 285

His Thr Arg Gly Leu Asp Phe Ala Cys Asp Ile Tyr Ile Trp Ala Pro
    290                 295                 300

Leu Ala Gly Thr Cys Gly Val Leu Leu Leu Ser Leu Val Ile Thr Leu
305                 310                 315                 320
```

```
Tyr Cys Lys Arg Gly Arg Lys Lys Leu Leu Tyr Ile Phe Lys Gln Pro
                325                 330                 335

Phe Met Arg Pro Val Gln Thr Thr Gln Glu Asp Gly Cys Ser Cys
            340                 345                 350

Arg Phe Pro Glu Glu Glu Glu Gly Cys Glu Leu Arg Val Lys Phe
            355                 360                 365

Ser Arg Ser Ala Asp Ala Pro Ala Tyr Lys Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
                420                 425                 430

Glu Ala Tyr Ser Glu Ile Gly Met Lys Gly Glu Arg Arg Arg Gly Lys
                435                 440                 445

Gly His Asp Gly Leu Tyr Gln Gly Leu Ser Thr Ala Thr Lys Asp Thr
                450                 455                 460

Tyr Asp Ala Leu His Met Gln Ala Leu Pro Pro Arg
465                 470                 475
```

<210> SEQ ID NO 91
<211> LENGTH: 1437
<212> TYPE: DNA
<213> ORGANISM: Artificial Sequence
<220> FEATURE:
<223> OTHER INFORMATION: HLA-A2/HPV16E7(11-19) 17363 ScFv (VL-VH) CAR-T
      (Irrelevant Control)
      (17363_ULC-VK(1)(human).G4Sx3_4.17363_VH(human).
      G4S_V2.hCD8a hinge/TM.hCD137 (4-1BB).hCD3 zeta)

<400> SEQUENCE: 91

```
gacatccaga tgacccagtc tccatcctcc ctgtctgcat ctgtaggaga cagagtcacc      60
atcacttgcc gggcaagtca gagcattagc agctatttaa attggtatca cagaaaacca    120
gggaaagccc ctaagctcct gatctatgct gtttccattt tgcaaagtgg ggtcccatca    180
aggttcagtg gcagtggatc tgggacagat ttcactctca ccatcaactc tctgcaacct    240
gaagattttg caacttactc ctgtcaacag acttacagta cccctccgat caccttcggc    300
caagggacac gactggagat taaaggtgga ggcggtagtg gcggaggcgg aagtggtgga    360
ggaggctcag aggtgcagct gttggagtct gggggaggct tggtacaacc tggggggtcc    420
ctgagactct cctgtgcagc ctctggattc acctttagca gttatgccat gacctgggtc    480
cgccaggctc cagggatggg actggagtgg gtctcagtta ttagtggtag tggtagtgaa    540
acatactacg cagactccgt gaagggccgg ttcaccatct ccagagacaa ttccaaaaac    600
acactgtatc tgcaaatgaa cagcctgaga gccgaagaca cggccgtata ttactgtgtg    660
aaagattctt cgtataggag ctcgtcgagg cctactacta ctacggaat ggacgtctgg     720
ggcctaggga ccacggtcac cgtctcctca ggaggtggtg aagtactac cactcctgct     780
ccccgccccc caacacctgc tccaactatt gcatcccaac cactctccct cagacccgaa    840
gcttgtcgcc ccgccgccgg aggtgctgtt cacactagag gactcgattt tgcttgcgac    900
atttatatct gggcccact tgcaggtact tgcggagtat tgctgctctc acttgttatt     960
actctttatt gcaaacgggg cagaaagaaa ctcctgtata tattcaaaca accatttatg   1020
agaccagtac aaactactca gaggaagat ggctgtagct gccgatttcc agaagaagaa    1080
```

```
gaaggaggat gtgaactgag agtgaagttc agcaggagcg cagacgcccc cgcgtacaag    1140
cagggccaga accagctcta taacgagctc aatctaggac gaagagagga gtacgatgtt    1200
ttggacaaga gacgtggccg ggaccctgag atggggggaa agccgagaag gaagaaccct    1260
caggaaggcc tgtacaatga actgcagaaa gataagatgg cggaggccta cagtgagatt    1320
gggatgaaag gcgagcgccg gaggggcaag gggcacgatg gcctttacca gggtctcagt    1380
acagccacca aggacaccta cgacgcccct cacatgcagg ccctgccccc tcgctaa      1437
```

<210> SEQ ID NO 92
<211> LENGTH: 478
<212> TYPE: PRT
<213> ORGANISM: Artificial Sequence
<220> FEATURE:
<223> OTHER INFORMATION: HLA-A2/HPV16E7(11-19) 17363 ScFv (VL-VH) CAR-T
      (Irrelevant Control)
      (17363_ULC-VK(1)(human).G4Sx3_4.17363_VH(human).
      G4S_V2.hCD8a hinge/TM.hCD137 (4-1BB).hCD3 zeta)

<400> SEQUENCE: 92

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Val Ser Ile Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Ser Cys Gln Gln Thr Tyr Ser Thr Pro Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Ser Glu Val Gln Leu Leu
        115                 120                 125

Glu Ser Gly Gly Gly Leu Val Gln Pro Gly Gly Ser Leu Arg Leu Ser
    130                 135                 140

Cys Ala Ala Ser Gly Phe Thr Phe Ser Ser Tyr Ala Met Thr Trp Val
145                 150                 155                 160

Arg Gln Ala Pro Gly Met Gly Leu Glu Trp Val Ser Val Ile Ser Gly
                165                 170                 175

Ser Gly Ser Glu Thr Tyr Tyr Ala Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Arg Ala Glu Asp Thr Ala Val Tyr Tyr Cys Val Lys Asp Ser Ser
    210                 215                 220

Tyr Arg Ser Ser Arg Ala Tyr Tyr Tyr Gly Met Asp Val Trp
225                 230                 235                 240

Gly Leu Gly Thr Thr Val Thr Val Ser Ser Gly Gly Gly Gly Ser Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
        275                 280                 285
```

```
Ala Val His Thr Arg Gly Leu Asp Phe Ala Cys Asp Ile Tyr Ile Trp
            290                 295                 300

Ala Pro Leu Ala Gly Thr Cys Gly Val Leu Leu Ser Leu Val Ile
305                 310                 315                 320

Thr Leu Tyr Cys Lys Arg Gly Arg Lys Lys Leu Leu Tyr Ile Phe Lys
                325                 330                 335

Gln Pro Phe Met Arg Pro Val Gln Thr Thr Gln Glu Glu Asp Gly Cys
                340                 345                 350

Ser Cys Arg Phe Pro Glu Glu Glu Gly Gly Cys Glu Leu Arg Val
            355                 360                 365

Lys Phe Ser Arg Ser Ala Asp Ala Pro Ala Tyr Lys Gln Gly Gln Asn
                370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
                420                 425                 430

Met Ala Glu Ala Tyr Ser Glu Ile Gly Met Lys Gly Glu Arg Arg Arg
                435                 440                 445

Gly Lys Gly His Asp Gly Leu Tyr Gln Gly Leu Ser Thr Ala Thr Lys
450                 455                 460

Asp Thr Tyr Asp Ala Leu His Met Gln Ala Leu Pro Pro Arg
465                 470                 475
```

<210> SEQ ID NO 93
<211> LENGTH: 5
<212> TYPE: PRT
<213> ORGANISM: Artificial Sequence
<220> FEATURE:
<223> OTHER INFORMATION: linker

<400> SEQUENCE: 93

```
Gly Gly Gly Gly Ser
1               5
```

<210> SEQ ID NO 94
<211> LENGTH: 10
<212> TYPE: PRT
<213> ORGANISM: Artificial Sequence
<220> FEATURE:
<223> OTHER INFORMATION: linker

<400> SEQUENCE: 94

```
Gly Gly Gly Gly Ser Gly Gly Gly Gly Ser
1               5                   10
```

<210> SEQ ID NO 95
<211> LENGTH: 15
<212> TYPE: PRT
<213> ORGANISM: Artificial Sequence
<220> FEATURE:
<223> OTHER INFORMATION: linker

<400> SEQUENCE: 95

```
Gly Gly Gly Gly Ser Gly Gly Gly Gly Ser Gly Gly Gly Gly Ser
1               5                   10                  15
```

<210> SEQ ID NO 96
<211> LENGTH: 18

```
<212> TYPE: PRT
<213> ORGANISM: Artificial Sequence
<220> FEATURE:
<223> OTHER INFORMATION: linker

<400> SEQUENCE: 96

Gly Ser Thr Ser Gly Ser Gly Lys Pro Gly Ser Gly Glu Gly Ser Thr
1               5                   10                  15

Lys Gly

<210> SEQ ID NO 97
<211> LENGTH: 45
<212> TYPE: PRT
<213> ORGANISM: Artificial Sequence
<220> FEATURE:
<223> OTHER INFORMATION: hinge

<400> SEQUENCE: 97

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 98
<211> LENGTH: 24
<212> TYPE: PRT
<213> ORGANISM: Artificial Sequence
<220> FEATURE:
<223> OTHER INFORMATION: TM domain

<400> SEQUENCE: 98

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 99
<211> LENGTH: 42
<212> TYPE: PRT
<213> ORGANISM: Artificial Sequence
<220> FEATURE:
<223> OTHER INFORMATION: 4-1BB

<400> SEQUENCE: 99

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 100
<211> LENGTH: 112
<212> TYPE: PRT
<213> ORGANISM: Artificial Sequence
<220> FEATURE:
<223> OTHER INFORMATION: cd3-Zeta

<400> SEQUENCE: 100

Arg Val Lys Phe Ser Arg Ser Ala Asp Ala Pro Ala Tyr Lys Gln Gly
1               5                   10                  15
```

```
Gln Asn Gln Leu Tyr Asn Glu Leu Asn Leu Gly Arg Arg Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 101
<211> LENGTH: 184
<212> TYPE: PRT
<213> ORGANISM: Artificial Sequence
<220> FEATURE:
<223> OTHER INFORMATION: human BCMA (TNFRSF17) Protein NP_001183.2

<400> SEQUENCE: 101

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
        50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
                100                 105                 110

Ile Ile Leu Pro Arg Gly Leu Glu Tyr Thr Val Glu Glu Cys Thr Cys
            115                 120                 125

Glu Asp Cys Ile Lys Ser Lys Pro Lys Val Asp Ser Asp His Cys Phe
        130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
                180
```